US005468639A

United States Patent [19]

Fasano et al.

[11] Patent Number: 5,468,639

[45] Date of Patent: Nov. 21, 1995

[54] **ISOLATED DNA MOLECULE ENCODING SHET2 OF *SHIGELLA FLEXNERI* 2A**

[75] Inventors: Alessio Fasano, Ellicott City; Myron M. Levine, Columbia; James P. Nataro, Catonsville; Fernando Noriega, Columbia, all of Md.

[73] Assignee: University of Maryland at Baltimore, Baltimore, Md.

[21] Appl. No.: 160,317

[22] Filed: Dec. 2, 1993

Related U.S. Application Data

[63] Continuation-in-part of Ser. No. 894,774, Jun. 5, 1992, abandoned.

[51] Int. Cl.[6] .......................... C12N 15/00; C07H 19/00; C07H 21/00; C12P 21/04

[52] U.S. Cl. .................... 435/320.1; 435/71.1; 435/71.3; 424/93.2; 530/350; 530/825; 536/22.1; 536/23.1; 536/23.7

[58] Field of Search ................................ 435/71.1, 71.3, 435/320.1; 530/350, 825; 536/22.1, 23.1, 23.7; 424/93.2

[56] References Cited

U.S. PATENT DOCUMENTS 5,204,097 4/1993 Arnon et al. ............................ 424/92

OTHER PUBLICATIONS

Glover, "Principles of Cloning DNA", *Gene Cloning* pp. 1–20 1984.

Lee et al. "Generation of cDNA Probes . . . " *Science* vol. 239, pp. 1288–1291 Mar. 11, 1988.

Fasano et al, *J. Pediatr. Gastroenterol. Nutr.*, 13:320 (1991).

Fasano et al, *Infect. Immun.*, 58(11):3717–3723 (1990).

Maurer et al, *Methods in Enzymology*, 70:49–70 (1980).

Strockbine et al, *Infect. Immun.*, 50(3):695–700 (1985).

Levine, *J. Inf. Dis.*, 155(3):377–389 (1987).

Fasano et al, "Elaboration of an Enterotoxin by *Shigella Flexneria* 2a", *Rivista Italian Di Pediatria*, 17(4):182 (Abstract) (Aug., 1991).

Lecture Slides, "Production by Enteroinvasive *E. coli* and *Shigella Flexneria* 2a of a Novel Enterotoxin Moiety", presented at Walter Reed Army Institute, Apr. 15, 1990.

Fasano et al, "Enterotoxic Factors Elaborated by *Shigella Flexneria* 2a", presented at the *29th U.S.–Japan Joint conference on Cholers and Related Diarrheal Diseases*, Dec. 2, 1992.

Nataro et al, "Cloning and Sequencing of a New Plasmid–Encoded Enterotoxin in Enteroinvasive *E. coli* and Shigella", presented at the *29th U.S.–Japan Joint Conference on Cholers and Related Diarrheal Diseases*, Dec. 2, 1992.

Noriega et al, "Construction and Characterization of Oral Attenuated Shigella Vaccine–Candidates and their Potential Use as Live Vector–Hyrbrid Vaccines", presented at the *29th U.S.–Japan Joint Conference on Cholera and Related Diarrheal Diseases*, Dec. 2, 1992.

*Primary Examiner*—Robert A. Wax
*Assistant Examiner*—Hyosuk Kim
*Attorney, Agent, or Firm*—Sughrue, Mion, Zinn, Macpeak & Seas

[57] ABSTRACT

Substantially pure enterotoxins of *Shigella flexneri* 2a are described, along with a method for obtaining the same, antibodies having binding specificity to the enterotoxins and a method for use of the enterotoxins to develop a non-reactogenic *Shigella flexneri* 2a vaccine candidate.

4 Claims, 13 Drawing Sheets

FIGURE 6A

ATCGATATAT TGTTTATTGT CAGTATGGCT CAATGTGATA 40

ATAGTTGGAA AGTTTGATGG GTTTCGCCCC GTTGTAGCGG 80

TAGTCGACCC CGTTGTAGCG GTAGTCGAGC TGGAAGGTCT 120

TCAGGCACTG CTTACAGCGA TAGAGCAGCC CCCCAGAACT 160

GGAATGGCCG TTCCGATACC CCCCTGAGTT TCAGAGTAAC 200

GGGGACAAAC CACATCAATC TTTGCCATCA ATCATCCAAA 240

GGGCAAAGAG TACAACAACA CTAAGTCTGC GTCACAACCC 280

ATCAATGAAA GGAATATATA CAT ATG CCA TCA GTA ATT 318
Met Pro Ser Val Asn
1 5

TTA ATC CCA TCA AGG AAA ATA TGT TTG CAA AAT ATG 354
Leu Ile Pro Ser Arg Lys Ile Cys Leu Gln Asn Met
10 15

ATA AAT AAA GAC AAC GTC TCT GTT GAG ACA ATC CAG 390
Ile Asn Lys Asp Asn Val Ser Val Glu Thr Ile Gln
20 25

TCT CTA TTG CAC TCA AAA CAA TTG CCA TAT TTT TCT 426
Ser Leu Leu His Ser Lys Gln Leu Pro Tyr Phe Ser
30 35 40

GAC AAG AGG AGT TTT TTA TTA AAT CTA AAT TGC CAA 462
Asp Lys Arg Ser Phe Leu Leu Asn Leu Asn Cys Gln
45 50

GTT ACC GAT CAC TCT GGA AGA CTT ATT GTC TGT CGA 498
Val Thr Asp His Ser Gly Arg Leu Ile Val Cys Arg
55 60 65

CAT TTA GCT TCC TAC TGG ATA GCA CAG TTT AAC AAA 534
His Leu Ala Ser Tyr Trp Ile Ala Gln Phe Asn Lys
70 75

AGT AGT GGT CAC GTG GAT TAT CAT CAC TTT GCT TTT 570
Ser Ser Gly His Val Asp Tyr His His Phe Ala Phe
80 85

CCG GAT GAA ATT AAA AAT TAT GTT TCA GTG AGT GAA 606
Pro Asp Glu Ile Lys Asn Tyr Val Ser Val Ser Glu
90 95 100

FIGURE 6B

```
GAA GAA AAG GCT ATT AAT GTG CCT GCT ATT ATT TAT    642
Glu Glu Lys Ala Ile Asn Val Pro Ala Ile Ile Tyr
            105                 110

TTT GTT GAA AAC GGT TCA TGG GGA GAT ATT ATT TTT    678
Phe Val Glu Asn Gly Ser Trp Gly Asp Ile Ile Phe
    115                 120                 125

TAT ATT TTC AAT GAA ATG ATT TTT CAT TCC GAA AAA    714
Tyr Ile Phe Asn Glu Met Ile Phe His Ser Glu Lys
                130                 135

AGC AGA GCA CTA GAA ATA AGT ACA TCA AAT CAC AAT    750
Ser Arg Ala Leu Glu Ile Ser Thr Ser Asn His Asn
        140                 145

ATG GCA TTA GGC TTG AAG ATT AAA GAA ACT AAA AAT    786
Met Ala Leu Gly Leu Lys Ile Lys Glu Thr Lys Asn
150                 155                 160

GGG GGG GAT TTT GTC ATT CAG CTT TAT GAT CCC AAC    822
Gly Gly Asp Phe Val Ile Gln Leu Tyr Asp Pro Asn
            165                 170

CAT ACA GCA ACT CAT TTA CGA GCA GAG TTT AAC AAA    858
His Thr Ala Thr His Leu Arg Ala Glu Phe Asn Lys
    175                 180                 185

TTT AAC TTA GCT AAA ATA AAA AAA CTG ACT GTA GAT    894
Phe Asn Leu Ala Lys Ile Lys Lys Leu Thr Val Asp
                190                 195

AAT TTT CTT GAT GAA AAA CAT CAG AAA TGT TAT GGT    930
Asn Phe Leu Asp Glu Lys His Gln Lys Cys Tyr Gly
        200                 205

CTT ATA TCC GAC GGT ATG TCT ATA TTT GTG GAC AGA    966
Leu Ile Ser Asp Gly Met Ser Ile Phe Val Asp Arg
210                 215                 220

CAT ACT CCA ACA AGC ATG TCC TCC ATA ATC AGA TGG   1002
His Thr Pro Thr Ser Met Ser Ser Ile Ile Arg Trp
            225                 230

CCT AAT AAT TTA CTT CAC CCC AAA GTT ATT TAT CAC   1038
Pro Asn Asn Leu Leu His Pro Lys Val Ile Tyr His
    235                 240                 245

GCG ATG CGT ATG GGA TTG ACT GAG CTA ATC CAA AAA   1074
Ala Met Arg Met Gly Leu Thr Glu Leu Ile Gln Lys
                250                 255
```

FIGURE 6C

| | | | | | | | | | | | | |
|---|---|---|---|---|---|---|---|---|---|---|---|---|
| GTA | ACA | AGA | GTC | GTA | CAA | CTA | TCT | GAC | CTT | TCA | GAC | 1110 |
| Val | Thr | Arg | Val | Val | Gln | Leu | Ser | Asp | Leu | Ser | Asp | |
| | | 260 | | | | | 265 | | | | | |
| AAT | ACG | TTA | GAA | TTA | CTT | TTG | GCA | GCC | AAA | AAT | GAC | 1146 |
| Asn | Thr | Leu | Glu | Leu | Leu | Leu | Ala | Ala | Lys | Asn | Asp | |
| 270 | | | | | 275 | | | | | 280 | | |
| GAT | GGT | TTG | TCA | GGA | TTG | CTT | TTA | GCT | TTA | CAA | AAT | 1182 |
| Asp | Gly | Leu | Ser | Gly | Leu | Leu | Leu | Ala | Leu | Gln | Asn | |
| | | | 285 | | | | | 290 | | | | |
| GGG | CAT | TCA | GAT | ACA | ATC | TTA | GCA | TAC | GGA | GAA | CTC | 1218 |
| Gly | His | Ser | Asp | Thr | Ile | Leu | Ala | Tyr | Gly | Glu | Leu | |
| | 295 | | | | | 300 | | | | | 305 | |
| CTG | GAA | ACT | TCT | GGA | CTT | AAC | CTT | GAT | AAA | ACG | GTA | 1254 |
| Leu | Glu | Thr | Ser | Gly | Leu | Asn | Leu | Asp | Lys | Thr | Val | |
| | | | | 310 | | | | | 315 | | | |
| GAA | CTA | CTA | ACT | GCG | GAA | GGA | ATG | GGA | GGA | CGA | ATA | 1290 |
| Glu | Leu | Leu | Thr | Ala | Glu | Gly | Met | Gly | Gly | Arg | Ile | |
| | | 320 | | | | | 325 | | | | | |
| TCG | GGT | TTA | TCC | CAA | GCA | CTT | CAA | AAT | GGG | CAT | GCA | 1326 |
| Ser | Gly | Leu | Ser | Gln | Ala | Leu | Gln | Asn | Gly | His | Ala | |
| 330 | | | | | 335 | | | | | 340 | | |
| GAA | ACT | ATC | AAA | ACA | TAC | GGA | AGG | CTT | CTC | AAG | AAG | 1362 |
| Glu | Thr | Ile | Lys | Thr | Tyr | Gly | Arg | Leu | Leu | Lys | Lys | |
| | | | 345 | | | | | 350 | | | | |
| AGA | GCA | ATA | AAT | ATC | GAA | TAC | AAT | AAG | CTG | AAA | AAT | 1398 |
| Arg | Ala | Ile | Asn | Ile | Glu | Tyr | Asn | Lys | Leu | Lys | Asn | |
| | 355 | | | | | 360 | | | | | 365 | |
| TTG | CTG | ACC | GCT | TAT | TAT | TAT | GAT | GAA | GTA | CAC | AGA | 1434 |
| Leu | Leu | Thr | Ala | Tyr | Tyr | Tyr | Asp | Glu | Val | His | Arg | |
| | | | | 370 | | | | | 375 | | | |
| CAG | ATA | CCT | GGA | CTA | ATG | TTT | GCT | CTT | CAA | AAT | GGA | 1470 |
| Gln | Ile | Pro | Gly | Leu | Met | Phe | Ala | Leu | Gln | Asn | Gly | |
| | | 380 | | | | | 385 | | | | | |
| CAT | GCA | GAT | GCT | ATA | CGC | GCA | TAC | GGT | GAG | CTC | ATT | 1506 |
| His | Ala | Asp | Ala | Ile | Arg | Ala | Tyr | Gly | Glu | Leu | Ile | |
| 390 | | | | | 395 | | | | | 400 | | |
| CTT | AGC | CCC | CCT | CTC | CTC | AAC | TCA | GAG | GAT | ATT | GTA | 1542 |
| Leu | Ser | Pro | Pro | Leu | Leu | Asn | Ser | Glu | Asp | Ile | Val | |
| | | | 405 | | | | | 410 | | | | |

FIGURE 6D

```
AAT TTG CTG GCC TCA AGG AGA TAT GAC AAT GTT CCC  1578
Asn Leu Leu Ala Ser Arg Arg Tyr Asp Asn Val Pro
    415                 420                 425

GGA CTT CTG TTA GCA TTG AAT AAT GGA CAG GCT GAT  1614
Gly Leu Leu Leu Ala Leu Asn Asn Gly Gln Ala Asp
                430                 435

GCA ATC TTA GCT TAT GGT GAT ATC TTG AAT GAG GCA  1650
Ala Ile Leu Ala Tyr Gly Asp Ile Leu Asn Glu Ala
        440                 445

AAA CTT AAC TTG GAT AAA AAA GCA GAG CTG TTA GAA  1686
Lys Leu Asn Leu Asp Lys Lys Ala Glu Leu Leu Glu
450                 455                 460

GCG AAA GAT TCT AAT GGT TTA TCT GGA TTG TTT GTA  1722
Ala Lys Asp Ser Asn Gly Leu Ser Gly Leu Phe Val
            465                 470

GCC TTG CAT AAT GGA TGT GTA GAA ACA ATT ATT GCT  1758
Ala Leu His Asn Gly Cys Val Glu Thr Ile Ile Ala
    475                 480                 485

TAT GGG AAA ATA CTT CAC ACT GCA GAC CTT ACT CCA  1794
Tyr Gly Lys Ile Leu His Thr Ala Asp Leu Thr Pro
                490                 495

CAT CAG GCA TCA AAA TTA CTG GCA GCA GAA GGC CCA  1830
His Gln Ala Ser Lys Leu Leu Ala Ala Glu Gly Pro
        500                 505

AAT GGG GTA TCT GGA TTA ATT ATA GCT TTT CAA AAT  1866
Asn Gly Val Ser Gly Leu Ile Ile Ala Phe Gln Asn
510                 515                 520

AGG AAT TTT GAG GCA ATA AAA ACT TAT ATG GGA ATA  1902
Arg Asn Phe Glu Ala Ile Lys Thr Tyr Met Gly Ile
            525                 530

ATA AAA AAT GAA AAT ATT ACA CCT GAA GAA ATA GCA  1938
Ile Lys Asn Glu Asn Ile Thr Pro Glu Glu Ile Ala
    535                 540                 545

GAA CAC TTG GAC AAA AAA AAT GGA AGT GAT TTT CTA  1974
Glu His Leu Asp Lys Lys Asn Gly Ser Asp Phe Leu
                550                 555

GAA ATT ATG AAG AAT ATA AAA AGC TGAATATTAT        2008
Glu Ile Met Lys Asn Ile Lys Ser
        560                 565
```

FIGURE 7A

```
ACCCATCAAT GAAAGGAATA TATA CAT ATG CCA TCA GTA       39
                               Met Pro Ser Val
                                1

AAT TTA ATC CCA TCA AGG AAA ATA TGT TTG CAA AAT      75
Asn Leu Ile Pro Ser Arg Lys Ile Cys Leu Gln Asn
 5                  10                  15

ATG ATA AAT AAA GAC AAC GTC TCT GTT GAG ACA ATC     111
Met Ile Asn Lys Asp Asn Val Ser Val Glu Thr Ile
            20                  25

CAG TCT CTA TTG CAC TCA AAA CAA TTG CCA TAT TTT     147
Gln Ser Leu Leu His Ser Lys Gln Leu Pro Tyr Phe
    30                  35                  40

TCT GAC AAG AGG AGT TTT TTA TTA AAT CTA AAT TGC     183
Ser Asp Lys Arg Ser Phe Leu Leu Asn Leu Asn Cys
                45                  50

CAA GTT ACC GAT CAC TCT GGA AGA CTT ATT GTC TGT     219
Gln Val Thr Asp His Ser Gly Arg Leu Ile Val Cys
        55                  60

CGA CAT TTA GCT TCC TAC TGG ATA GCA CAG TTT AAC     255
Arg His Leu Ala Ser Tyr Trp Ile Ala Gln Phe Asn
65                  70                  75

AAA AGT AGT GGT CAC GTG GAT TAT CAT CAC TTT GCT     291
Lys Ser Ser Gly His Val Asp Tyr His His Phe Ala
            80                  85

TTT CCG GAT GAA ATT AAA AAT TAT GTT TCA GTG AGT     327
Phe Pro Asp Glu Ile Lys Asn Tyr Val Ser Val Ser
    90                  95                  100

GAA GAA GAA AAG GCT ATT AAT GTG CCT GCT ATT ATT     363
Glu Glu Glu Lys Ala Ile Asn Val Pro Ala Ile Ile
                105                 110

TAT TTT GTT GAA AAC GGT TCA TGG GGA GAT ATT ATT     399
Tyr Phe Val Glu Asn Gly Ser Trp Gly Asp Ile Ile
        115                 120

TTT TAT ATT TTC AAT GAA ATG ATT TTT CAT TCC GAA     435
Phe Tyr Ile Phe Asn Glu Met Ile Phe His Ser Glu
125                 130                 135

AAA AGC AGA GCA CTA GAA ATA AGT ACA TCA AAT CAC     471
Lys Ser Arg Ala Leu Glu Ile Ser Thr Ser Asn His
            140                 145
```

FIGURE 7B

AAT ATG GCA TTA GGC TTG AAG ATT AAA GAA ACT AAA 507
Asn Met Ala Leu Gly Leu Lys Ile Lys Glu Thr Lys
150 155 160

AAT GGG GGG GAT TTT GTC ATT CAG CTT TAT GAT CCC 543
Asn Gly Gly Asp Phe Val Ile Gln Leu Tyr Asp Pro
165 170

AAC CAT ACA GCA ACT CAT TTA CGA GCA GAG TTT AAC 579
Asn His Thr Ala Thr His Leu Arg Ala Glu Phe Asn
175 180

AAA TTT AAC TTA GCT AAA ATA AAA AAA CTG ACT GTA 615
Lys Phe Asn Leu Ala Lys Ile Lys Lys Leu Thr Val
185 190 195

GAT AAT TTT CTT GAT GAA AAA CAT CAG AAA TGT TAT 651
Asp Asn Phe Leu Asp Glu Lys His Gln Lys Cys Tyr
200 205

GGT CTT ATA TCC GAC GGT ATG TCT ATA TTT GTG GAC 687
Gly Leu Ile Ser Asp Gly Met Ser Ile Phe Val Asp
210 215 220

AGA CAT ACT CCA ACA AGC ATG TCC TCC ATA ATC AGA 723
Arg His Thr Pro Thr Ser Met Ser Ser Ile Ile Arg
225 230

TGG CCT GAT AAT TTA CTT CAC CCC AAA GTT ATT TAT 759
Trp Pro Asp Asn Leu Leu His Pro Lys Val Ile Tyr
235 240

CAC GCG ATG CGT ATG GGA TTG ACT GAG CTA ATC CAA 795
His Ala Met Arg Met Gly Leu Thr Glu Leu Ile Gln
245 250 255

AAA GTA ACA AGA GTC GTA CAA CTA TCT GAC CTT TCA 831
Lys Val Thr Arg Val Val Gln Leu Ser Asp Leu Ser
260 265

GAC AAT ACG TTA GAA TTA CTT TTG GCA GCC AAA AAT 867
Asp Asn Thr Leu Glu Leu Leu Leu Ala Ala Lys Asn
270 275 280

GAC GAT GGT TTG TCA GGA TTG CTT TTA GCT TTA CAA 903
Asp Asp Gly Leu Ser Gly Leu Leu Leu Ala Leu Gln
285 290

AAT GGG CAT TCA GAT ACA ATC TTA GCA TAC GGA GAA 939
Asn Gly His Ser Asp Thr Ile Leu Ala Tyr Gly Glu
295 300

FIGURE 7C

CTC TTG GAA ACT TCT GGA CTT AAC CTT GAT AAA ACG 975
Leu Leu Glu Thr Ser Gly Leu Asn Leu Asp Lys Thr
305 310 315

GTA GAA CTA CTA ACT GCG GAA GGA ATG GGA GGA CGA 1011
Val Glu Leu Leu Thr Ala Glu Gly Met Gly Gly Arg
320 325

ATA TCG GGT TTA TCC CAA GCA CTT CAA AAT GGG CAT 1047
Ile Ser Gly Leu Ser Gln Ala Leu Gln Asn Gly His
330 335 340

GCA GAA ACT ATC AAA ACA TAC GGA AGG CTT CTC AAG 1083
Ala Glu Thr Ile Lys Thr Tyr Gly Arg Leu Leu Lys
345 350

AAG AGA GCA ATA AAT ATC GAA TAC AAT AAG CTG AAA 1119
Lys Arg Ala Ile Asn Ile Glu Tyr Asn Lys Leu Lys
355 360

AAT TTG CTG ACC GCT TAT TAT TAT GAT GAA GTA CAC 1155
Asn Leu Leu Thr Ala Tyr Tyr Tyr Asp Glu Val His
365 370 375

AGA CAG ATA CCC GGA CTA ATG TTT GCT CTT CAA AAT 1191
Arg Gln Ile Pro Gly Leu Met Phe Ala Leu Gln Asn
380 385

GGA CAT GCA GAT GCT ATA CGC GCA TAC GGT GAG CTC 1227
Gly His Ala Asp Ala Ile Arg Ala Tyr Gly Glu Leu
390 395 400

ATT CTT AGC CCC CCT CTC CTC AAC TCA GAG GAT ATT 1263
Ile Leu Ser Pro Pro Leu Leu Asn Ser Glu Asp Ile
405 410

GTA AAT TTG CTG GCC TCA AGG AGA TAT GAC AAT GTT 1299
Val Asn Leu Leu Ala Ser Arg Arg Tyr Asp Asn Val
415 420

CCC GGA CTT CTG TTA GCA TTG AAT AAT GGA CAG GCT 1335
Pro Gly Leu Leu Leu Ala Leu Asn Asn Gly Gln Ala
425 430 435

GAT GCA ATC TTA GCT TAT GGT GAT ATC TTG AAT GAG 1371
Asp Ala Ile Leu Ala Tyr Gly Asp Ile Leu Asn Glu
440 445

GCA AAA CTT AAC TTG GAT AAA AAA GCA GAG CTG TTA 1407
Ala Lys Leu Asn Leu Asp Lys Lys Ala Glu Leu Leu
450 455 460

FIGURE 7D

```
GAA GCG AAA GAT TCT AAT GGT TTA TCT GGA TTG TTT  1443
Glu Ala Lys Asp Ser Asn Gly Leu Ser Gly Leu Phe
                465                 470

GTA GCC TTG CAT AAT GGA TGT GTA GAA ACA ATT ATT  1479
Val Ala Leu His Asn Gly Cys Val Glu Thr Ile Ile
        475                 480

GCT TAT GGG AAA ATA CTT CAC ACT GCA GAC CTT ACT  1515
Ala Tyr Gly Lys Ile Leu His Thr Ala Asp Leu Thr
485                 490                 495

CCA CAT CAG GCA TCA AAA TTA CTG GCA GCA GAA GGC  1551
Pro His Gln Ala Ser Lys Leu Leu Ala Ala Glu Gly
            500                 505

CCA AAT GGG GTA TCT GGA TTA ATT ATA GCT TTT CAA  1587
Pro Asn Gly Val Ser Gly Leu Ile Ile Ala Phe Gln
    510                 515                 520

AAT AGG AAT TTT GAG GCA ATA AAA ACT TAT ATG AAA  1623
Asn Arg Asn Phe Glu Ala Ile Lys Thr Tyr Met Lys
                525                 530

ATA ATA AAA AAT GAA AAT ATT ACA CCT GAA GAA ATA  1659
Ile Ile Lys Asn Glu Asn Ile Thr Pro Glu Glu Ile
        535                 540

GCA GAA CAC TTG GAC AAA AAA AAT GGA AGT GAT TTT  1695
Ala Glu His Leu Asp Lys Lys Asn Gly Ser Asp Phe
545                 550                 555

CTA GAA ATT ATG AAG AAT ATA AAA AGC              1722
Leu Glu Ile Met Lys Asn Ile Lys Ser
            560                 565
```

ISOLATED DNA MOLECULE ENCODING SHET2 OF *SHIGELLA FLEXNERI* 2A

CROSS-REFERENCE TO RELATED APPLICATIONS

This is a continuation-in-part of U.S. patent application Ser. No. 07/894,774, filed Jun. 5, 1992.

FIELD OF THE INVENTION

The present invention relates to two substantially pure enterotoxins of *Shigella flexneri* 2a (hereinafter "ShET1" and "ShET2"), a method for obtaining the same, antibodies having binding specificity to the enterotoxins and a method for use of the enterotoxins to develop a non-reactogenic *Shigella flexneri* 2a vaccine candidate.

BACKGROUND OF THE INVENTION

Much has been written about the molecular pathogenesis of Shigella with respect to the genes and gene products involved in their ability to invade epithelial cells, and thereby to cause dysentery (Makino et al, *Microb. Pathog.*, 5:267–274 (1988); Sansonetti et al, *Infect. Immun.*, 35:852–860 (1982); Hale et al, *Infect. Immun.*, 40:340–350 (1983); Pal et al,. *J. Clin. Microbiol.*, 27:561–563 (1989); and Venkatesan et al, *Proc. Nat'l. Acad. Sci.* U.S.A., 85:9317–9321 (1988)). In contrast, surprisingly little is known of the precise mechanisms by which Shigella cause watery diarrhea.

Although the cardinal feature of the pathogenesis of *Shigella flexneri* 2a infection involves the invasion of epithelial cells, because *Shigella flexneri* 2a can cause watery diarrhea, it has been hypothesized that *Shigella flexneri* 2a also produces an enterotoxin (Rout et al, *Gastroenterology*, 68:270–278 (1975); and Kinsey et al, *Infect. Immun.*, 14:368–371 (1976)). More specifically, the following observations have suggested the existence of enterotoxins in *Shigella flexneri* 2a:

1. Clinically in humans, *Shigella flexneri* 2a infections are usually characterized by a period of watery diarrhea that precedes the onset of scanty dysenteric stools of blood and mucus (DuPont et al, *J. Infect. Dis.*, 119:296–299 (1969); and Stoll et al, *J. Infect. Dis.*, 146:177–183 (1982)). In mild cases, only watery diarrhea may occur, leading to a clinical picture undistinguishable from that due to enterotoxingenic *E. coli* infection (Taylor et al, *J. Infect. Dis.*, 153:1132–1138 (1986); and Taylor et al, *J. Clin. Microbiol.*, 26:1362–1366 (1988)).
2. When Shigella are fed to monkeys, three clinical syndromes are seen (Route et al, *Gastroenterology*, 68:270–278 (1975)). Some monkeys develop only dysentery; some exhibit only watery diarrhea and some exhibit watery diarrhea and dysentery. In vivo perfusion studies by Rout et al, *Gastroenterology*, 68:270–278 (1975), showed that net transport of water into the lumen of the colon occurs in all ill animals. In contrast, only in the jejunum of monkeys with overt watery diarrhea (alone or followed by dysentery) does there occur net secretion of water, sodium and chloride ions; such net transport does not occur in the jejunum of monkeys manifesting dysentery without watery diarrhea. Net secretion in the jejunum was not accompanied by abnormal histological findings in this anatomic site of the small intestine.

3. The net secretion of water and electrolytes into the jejunum of monkeys with watery diarrhea requires the passage of Shigella through the jejunum (Kinsey et al, *Infect. Immun.*, 14:368–371 (1976)). This was demonstrated by bypassing the small intestine and inoculating Shigella directly into the cecum of monkeys. Of 16 monkeys who developed clinical illness, 15 manifested dysentery, "... only rarely preceded by mild diarrhea". Net secretion of water and sodium into the colon was recorded in ill monkeys that developed dysentery following intracecal inoculation, while no abnormalities of water or electrolyte transport were observed in the jejunum of the ill animals.

Together, these observations suggest that Shigella elaborate an enterotoxin that elicits secretion early in the infection as the organisms pass through the jejunum.

However, except for the cytotoxin/neurotoxin/enterotoxin elaborated by *Shigella dysenteriae* (O'Brien et al, *Microbiol. Rev.*, 5:206–220 (1987); Keusch et al, *Pharmac. Ther.*, 15:403–438 (1982); and Fontaine et al, *Infect. Immun.*, 56:3099–3109 (1988)), but not by other Shigella species, little convincing proof has been generated to substantiate the contention that Shigella, other than *Shigella dysenteriae*, in fact produce enterotoxins.

More specifically, previous attempts in the art to detect enterotoxic activity in supernatants of *Shigella flexneri* 2a have yielded positive findings in only one instance. O'Brien et al, *Infect. Immun.*, 15:796–798 (1977), partially purified a toxin produced by *Shigella flexneri* 2a strain M4243 that was 10 detectable in cell-free supernatants. This toxin stimulated fluid production in rabbit ileal loops, but was also cytotoxic for HeLa cells in monolayers and was lethal when inoculated intraperitoneally into mice. Further, it was not necessary to grow the bacteria in $Fe^{++}$-depleted medium in order to detect the enterotoxic activity. In addition, the cytotoxicity of the toxin described by O'Brien et al, supra, was neutralized by anti-sera to Shiga (*Shigella dysenteriae* 1) toxin.

Enterotoxic activity in cell-free supernatants of *Shigella flexneri* 2a and 3a was reported by Ketyi et al, *Acta Microbiol. Acad. Sci. Hung.*, 25:165–171 (1978); Ketyi et al, *Acta Microbiol. Acad. Sci. Hung.*, 25:219–227 (1978); and Ketyi et al, *Acta Microbiol. Acad. Sci. Hung.*, 25:319–325 (1978). Filtered ultrasonic lysates of two *Shigella flexneri* 2a and 3a strains were founds to give rapid fluid accumulation in rabbit ileal loops (4 hour assay). However, the loops showed no fluid accumulation when examined at 18–24 hours after inoculation. Only three loops were inoculated for each of the two test strains, and when examined at 4 hours, only ⅔ for one strain and ⅓ for the other strain were positive. In addition, the Shigella were not cultured in $Fe^{++}$-depleted medium.

In the present invention, it was discovered for the first time that enterotoxic activity, which is clearly dissociated from cytotoxic activity, is expressed by *Shigella flexneri* 2a in the bacteria-free culture supernatant, and could be detected only after growth of the bacteria in $Fe^{++}$-depleted medium.

It has been reported that when grown in $Fe^{++}$-depleted medium, enteroinvasive *Escherichia coli* (EIEC) elaborate an enterotoxin (MW circa 68–80 kDa) that causes fluid accumulation in isolated rabbit ileal loops and an electrical response in Ussing chambers (Fasano et al, *Infect. Immun.*, 58:3717–3723 (1990)). Based on the similarities known to exist between enteroinvasive *E. coli* and Shigella (Levine et al, *J. Infect. Dis.*, 155:377–389 (1987)), it was postulated in the present invention that *Shigella flexneri* 2a would express an enterotoxin when grown in $Fe^{++}$-depleted medium.

In the present invention, it was unexpectedly disclosed that *Shigella flexneri* 2a produces two distinct enterotoxins, one encoded by the chromosome, and the other encoded by an invasiveness virulent plasmid. The latter enterotoxin was found in the present invention to be essentially the same as the EIEC enterotoxin.

SUMMARY OF THE INVENTION

An object of the present invention is to purify the two enterotoxins produced by *Shigella flexneri* 2a.

Another object of the present invention is to provide a method for culturing *Shigella flexneri* 2a so as to produce said enterotoxins.

A further object of the present invention is to provide antibodies having binding specificity for said enterotoxins.

An additional object is to identify, clone and sequence the genes encoding such enterotoxins.

Still another object of the present invention is provide *Shigella flexneri* 2a mutants which fail to produce at least one functional enterotoxin as a result of a mutation in a Shigella enterotoxin gene.

These and other objects of the present invention have been achieved in the detailed description of the invention provided below.

BRIEF DESCRIPTION OF THE DRAWINGS

FIGS. 6A–6D (SEQ ID NO:1) show the DNA sequence of EIET enterotoxin encoded by enteroinvasive *E. coli,* as well as the determined amino acid sequence.

FIGS. 7A–7D (SEQ ID NO:2) show the DNA sequence of ShET2 enterotoxin located on the *Shigella flexneri* 2a invasiveness plasmid, as well as the determined amino acid sequence.

DETAILED DESCRIPTION OF THE INVENTION

Figure 1:
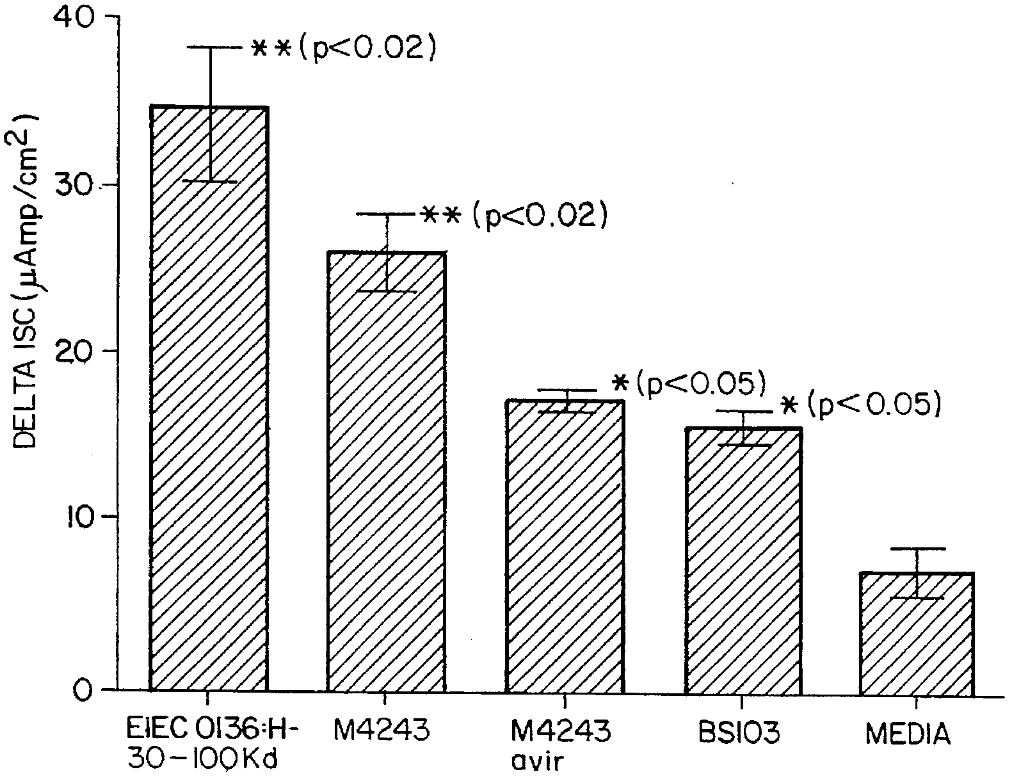
FIG. 1 shows the results of assays for enterotoxic activity in Ussing chambers when using culture supernatants of *Shigella flexneri* 2a strains M4243, M4243avir and BS103, the 30–100 kDa fraction of EIEC strain CVD/EI-34 (0136:H-) (as a positive control) and culture media (as a negative control). In these assays, variations in short-circuit current (delta Isc) were measured.

In the present invention, the enterotoxins are obtained by culturing *Shigella flexneri* 2a in $Fe^{++}$-depleted medium and collecting the supernatant.

"$Fe^{++}$-depleted media" is an expression well-known and used in the art. This expression refers to iron-depleted media, such as syncase broth, treated, e.g., in CHELEX® (BioRad), a styrene divinyl benzene resin matrix with iminodiacetic acid exchange groups, to leave just traces of iron in the medium.

The particular culture medium employed is not critical to the present invention. Examples of such culture media include $Fe^{++}$-depleted syncase broth or L-broth plus ethylenediamine-N-N'-diacetic acid (EDDA). $Fe^{++}$-depleted syncase broth is the preferred culture medium since maximal production of the enterotoxins was obtained with this medium.

While the culture temperature and incubation period are not critical to the present invention, generally the culturing temperature will range from 30° to 37° C. preferably 36° to 37° C., and the incubation period will range from 24 to 72 hours, preferably 48 to 72 hours.

The enterotoxins can be purified from the supernatant by size exclusion and HPLC chromatography.

*Shigella flexneri* 2a is a well-known virulent Shigella serotype available from a variety of sources, such as the Center for Vaccine Development, the Centers for Disease Control, the Walter Reed Army Institute of Research, the Uniformed Services University of the Health Sciences, and the Institut Pasteur. The particular strain of *Shigella flexneri* 2a employed in the present invention is not critical thereto. Examples of such *Shigella flexneri* 2a strains include M4243, M4243avir, *Shigella flexneri* 2a Chile 747, *Shigella flexneri* 2a Chile 3480 (Ferreccio et al, *Am. J. Epi.,* 134:614–627 (1991)), strain 2457T (Kotloff et al, *Infect. Immun.* 60:2218–2224 (1992)) and BS103 (Andrews et al, *Infect., Immun.,* 59:1997–2005 (1991)). The preferred *Shigella flexneri* 2a strains employed in the present invention is *Shigella flexneri* 2a strain M4243 and M4243avir.

*Shigella flexneri* 2a strain M4243 and its plasmid-cured derivative M4243avir can be obtained from, e.g., Dr. Samuel B. Formal of the Walter Reed Army Institute of Research, Washington, D.C. BS103 can be obtained from Dr. Anthony Maurelli of the Uniformed Services University of the Health Sciences, Bethesda, MD.

The antibodies having binding specificity to the two enterotoxins of the present invention may be polyclonal or monoclonal. Polyclonal antibodies to the purified enterotoxins can be prepared by conventional means as described in *Antibodies: A Laboratory Manual,* Harlow and Lane, Eds., Cold Spring Harbor Laboratory Press (1988). Monoclonal antibodies to the purified enterotoxins can be prepared by conventional means as described in Kohler et al, *Nature,* 256:495–497 (1975).

Monoclonal antibodies obtained using purified enterotoxins may be used to induce passive immunity against Shigella enteric infection. Such antibodies will bind the *Shigella flexneri* 2a enterotoxins, thus preventing their interaction with the cellular receptor, and preventing the stimulation of water and electrolyte secretion.

The substantially pure enterotoxins of the present invention are also useful for the development of a non-reactogenic *Shigella flexneri* 2a candidate live oral vaccine. As background, in the United States, *Shigella flexneri* 2a is one of the most common serotype of Shigella associated with disease. In developing countries of the world, *Shigella flexneri* is the most common serogroup of Shigella causing diarrheal disease and *Shigella flexneri* 2a is often the single most common serotype. Prospective epidemiologic studies in a low socioeconomic community in Santiago, Chile, where Shigella infections are endemic, have shown that an initial clinical episode of shigellosis confers significant protection against subsequent disease due to the same serotype (Ferroccio et al, *Am. J. Epidemiol.,* 134:614–627 (1991)). The immunizing effect of diarrheal illness due to wild-type Shigella has also been demonstrated in a volunteer model of experimental shigellosis where an initial clinical infection due to *Shigella flexneri* 2a (DuPont et al, *J. Infect. Dis.,* 125:12–16 (1972)) or *Shigella sonnei* (Herrington et al, *Vaccine,* 8:353–357 (1990)) conferred significant protection against re-challenge with the homologous wild-type organism. Together these observations suggest that it may be possible to protect against shigellosis with a vaccine that requires only a single dose.

There have been many attempts to develop attenuated strains of Shigella to serve as vaccinees. Some attempts have met with limited success. In the 1960s, streptomycin-dependent strains of *Shigella flexneri* 2a and other serotypes were developed and utilized as live oral vaccines (Mel et al, *Bull. WHO,* 32:647–655 (1965); Mel et al, Bull. WHO, 39:375–380 (1968); and Mel et al, *Acta Microbiol. Acad. Scient. Hung.,* 21:109–114 (1974)). These streptomycin-dependent strains were safe and conferred significant serotype-specific protection against shigellosis in most of the controlled field trials of efficacy that were carried out (Mel et al, *Bull. WHO,* 32:647–655 (1965); Mel et al, *Bull. WHO,* 39:375–380 (1968); Mel et al, *Acta Microbiol. Acad. Scient. Hung.,* 21:109–114 (1974); and Levine et al, *Am. J. Epidemiol.,* 133:424–429 (1976)). However, the streptomycin-dependent Shigella vaccines suffer from certain drawbacks. One is the fact that multiple spaced doses have to be given to confer protection (four doses over a two-week period containing large numbers ($2–4\times10^{10}$) of viable vaccine organisms). Moreover, protection is relatively short-lived. A booster dose has to be given after one year in order to maintain protection (Mel et al, *Acta Microbiol. Acad. Scient. Hung.,* 21:109–114 (1974)). Colonial mutant *Shigella flexneri* 2a vaccine strain $T_{32}$ described by Istrari et al, *Arch. Roumaines Pathol. Exp. Microbiol.,* 24:677–686 (1985), is also well-tolerated and protective (Wang Bing Rui, Arch. Roumaines pathol. Exp. Microbiol., 43:285–289 (1984)), but still requires multiple doses.

Because of the above-mentioned drawbacks of the streptomycin-dependent and $T_{32}$ vaccines of the 1960s, various investigators have attempted to make more immunogenic Shigella vaccines that can protect following the administration of just a single dose. The approaches taken have included:

(1) introducing specific segments of the chromosome of *E. coli* K-12 into Shigella by conjugation (Formal et al, *Dev. Bios. Stand.,* 15:73–78 (1971); and Levine et al, *J. Infect. DIS.,* 127:261–270 (1973));

(2) introducing DNA encoding protective Shigella antigens into *E. coli* K-12 (Formal et al, *Infect. Immun.,* 46:465–469 (1984)); and (3) inactivating genes of the aromatic amino acid biosynthesis pathway, thereby rendering the Shigella nutritionally dependent on substrates that are not available in human tissues (Lindberg et al, *Vaccine,* 6:146–150 (1988); and Karnell et al, *Rev. Infect. Dis.,* 13(4):S357–361 (1991)).

Regrettably, each of the above approaches has met with limitations. That is, hybrids in which Shigella carrying attenuating *E. coli* DNA are unstable, and can revert to full virulence (Levine et al, *J. Infect. Dis.,* 127:261–270 (1973)). Further, the most recent generation of *E. coli* expressing Shigella antigens has been associated with side reactions in vaccinees, including fever, mild diarrhea and every dysentery in some individuals (Kotloff et al, *J. Infect. Immun.,* 60:2218–2224 (1992)). Finally, some recipients of ΔaroD *Shigella flexneri* developed mild diarrhea (Karnell et al, *Rev. Infect Dis.,* 13(4):S357–361 (1991)). It has been hypothesized in the present application that the residual diarrhea encountered in these various *Shigella flexneri* candidate vaccine strains is likely due to the two enterotoxins.

Accordingly, *Shigella flexneri* 2a vaccine candidates can be constructed which, e.g., in addition to containing other attenuating mutations, express one or two toxoids, rather than the enterotoxins. This can be accomplished by deleting the portion of the enterotoxin genes that encodes the biologically active "toxic" site, leaving intact immunogenic sequences of the proteins.

More specifically, it is preferable to first construct a *Shigella flexneri* 2a strain in which deletion mutations are introduced in at least one aro gene (aroA, aroC, or aroD) of the Shigella chromosome, rendering the strain auxotrophic for para-aminobenzoic acid, a substrate that cannot be sufficiently scavenged in vivo in human. Strain CVD1202 prepared in Example 7 below contains an aroA deletion, and has been deposited at the American Type Culture Collection under ATCC No. 55517 on Dec. 1, 1993.

In addition, it is also preferable to have an independently attenuating, deletion mutation in the virG gene, which is found on the 140 MD invasiveness plasmid of *Shigella flexneri 2a.* This plasmid gene, also known as icsa (Sansonetti et al, *Vaccine,* 7:443–450 (1989)), is involved with the intracellular and intercellular spread of Shigella. This mutation is also present in CVD1202.

Recognizing that the vaccine candidate, e.g., CVD1202, may still not be sufficiently attenuated with just the aroA and VirG mutations (since the ability to produce enterotoxins remains intact), the enterotoxin genes can be mutated as a result of, e.g., the determination of the ShET1 and ShET2 gene sequences. One type of mutation, e.g., a deletion of substantially all of one or both of the enterotoxin genes, will totally inactivate enterotoxin production, resulting in a non-enterotoxinogenic strain. A second mutation, e.g., a deletion of part of one or both of the enterotoxin genes, will result in expression of toxoids, i.e., modified proteins that lacks the toxicity of the toxins but retain immunogenic moieties. This alternative mutation will result in a vaccine candidate strain that expresses, e.g., two toxoids. These toxoids can be used to induce active immunity against Shigella enteric infection.

The particular size of the deletion is not critical to the present invention, and can be readily determined based upon whether one desires to totally inactivate the enterotoxins, or simply produce toxoids.

The isolated DNA molecules of the present invention encoding the enterotoxin genes can be cloned in any suitable plasmid or vector, and used, e.g., to produce large amounts of DNA for use as probes or to integrate mutated enterotoxin genes into vaccine strains.

The expression "isolated" is used herein to mean set apart from its natural environment, e.g., the DNA molecules are separated from the parent chromosome or parent plasmid from which they were originally obtained in the present invention. Thus, "isolated" as used herein includes the presence of the DNA molecules in a foreign host or foreign plasmid.

The following examples are provided for illustrative purposes only and are in no way intended to limit the scope of the present invention.

EXAMPLE 1

Production of Enterotoxins

A. Preparation of Culture Filtrate Fraction

*Shigella flexneri* 2a strain M4243 and its plasmid-cured derivatives M4243avir and BS103, were grown overnight at 37° C. with shaking (200 rpm) in 5.0 ml of CHELEX® (BioRad, Richmond, Calif.) treated, $Fe^{++}$-depleted syncase broth (O'Brien et al, *J. Infect. Dis.*, 136:763–759 (1982)). CHELEX® binds to the iron present in the broth. All culture vessels employed were either new plastic or borosilicate glass soaked overnight in 6.0N HCl, and rinsed in distilled deionized water to ensure the absence of iron. 50 μl of the resulting culture broth were then subcultured in 5.0 ml of $Fe^{++}$-depleted syncase broth in baffled Fernbach flasks, and incubated for an additional 48 hours under the above conditions. After 72 hours of incubation, the cultures were harvested by centrifugation at 12,000 ×g for 20 minutes at 4° C. and the supernatants were passed through a 0.45 m filter membrane (Millipore Products, Bedford, Mass.) to obtain a "sterile supernatant".

B. Rabbit Ileal Loop Test

Whole cultures of *Shigella flexneri* 2a strain M4243 and its plasmid-cured derivative M4243avir, along with their respective sterile supernatants, obtained as described above, were tested in a standard rabbit ileal loop test. Supernatants of EIEC strain CVD/EI-34 (0136:H-) (which induces fluid accumulation in rabbit ileal loops), and non-pathogenic *E. coli* HS, were also included in each experiment as positive and negative controls, respectively (Fasano et al, *Infect. Immun.*, 58:3717–3723 (1991)). EIEC strain CVD/EI-34 (0136:H-) was obtained from the Center for Vaccine Development strain collection. *E. coli* HS was obtained from Dr. Herman Schneider, Walter Reed Army Institute of Research.

More specifically, male adult New Zealand white rabbits weighing 2–3 kg were starved for 24 hours but allowed water ad libitum. These animals were then anesthetized by intramuscular administration of a cocktail of 50 mg/kg ketamine and 1.0 mg/kg acepromazine, followed by intramuscular administration of 7.0 mg/kg xylazine.

Bacterial cultures were grown to reach 108–109 CFU/ml. Whole cultures, or the respective sterile supernatants, in a standard volume of 1.0 ml, were injected into the lumen of the intestine of the anesthetized rabbits near a tie closest to the mesoappendix (Moon et al, *Ann. N.Y. Acad. Sci.*, 176:197–211 (1971)); a second tie was made to isolate the site of inoculation. Proceeding proximally along the ileum, a series of five to six loops 7–8 cm long separated by double ties were isolated and inoculated (Moon et al, *Ann. N.Y. Acad. Sci.*, 176:197–211 (1971)). After 18 hours of incubation, the animals were sacrificed, the fluid volume and length of the loops were measured, and sections of intestine from each loop were fixed in 10% (v/v) formalinized saline and examined by light microscopy. The results of the loop test are shown in Experiment 1 in Table 1 below.

TABLE 1

| Fluid Accumulation (ml/cm) in Rabbit Ileal Loops | |
|---|---|
| Experiment 1 | |
| M4243 bacteria (5) | 1.06 ± 0.34* |
| M4243 supernatant (5) | 0.52 ± 0.10** |
| M4243avir bacteria (5) | 0.21 ± 0.50 |
| M4243avir supernatant (5) | 0.24 ± 0.09 |
| HS supernatant (5) | 0.09 ± 0.06 |
| Experiment 2 | |
| M4243 supernatants: | |
| L broth, 24 hours (4) | 0.01 ± 0.01 |
| L broth, 72 hours (4) | 0.04 ± 0.03 |
| Minimal $Fe^{++}$ broth, 24 hours (4) | 0.43 ± 0.11* |
| Minimal $Fe^{++}$ broth, 72 hours (4) | 0.47 ± 0.14* |
| HS supernatant: | |
| Minimal $Fe^{++}$ broth, 24 hours (4) | 0.01 ± 0.01 |

In the Table above, the results are expressed as mean ± SE for (n) animals. The bacterial cultures were grown for 72 hours unless otherwise indicated.
*p < 0.01 compared to HS;
**p < 0.05 compared to HS.

As shown in Experiment 1 in Table 1 above, the intestinal loops injected with the positive control, i.e., whole viable cultures of M4243, and sterile culture supernatant therefrom, showed pronounced fluid accumulation at 18 hours post-inoculation, with the whole viable culture showing a two-fold greater fluid accumulation. Further, as shown in Experiment 1 in Table 1 above, fluid accumulation induced by M4243avir (both whole culture and sterile supernatant) was slightly higher than the negative control strain HS.

The fluid to gut length recorded in the rabbit ileal loops, 0.5 ml/cm, measured using graduated syringes (fluid) and a scale (length), was substantially less than seen with enterohemorrhagic *E. coli* (EHEC) strain 933J, serotype (0157:H7), where ratios of 1.5–2.0 ml/cm occur. However, the recorded fluid to gut length measured using graduates syringes (fluid) and a scale (length) still represents definite evidence of net secretion and fluid accumulation. On histologic examination of the sections of intestine from each loop, severe tissue damage was observed with whole cultures of M4243, characterized by prominent necrosis of the luminal epithelium and marked villus atrophy. In contrast, with M4243 sterile culture supernatant, no tissue damage was detected. Further, no tissue damage was observed with whole cultures of M4243avir or sterile supernatants therefrom. Moreover, no tissue damage was observed with tissue incubated with the negative control strain HS.

To determine whether the time of incubation and the iron content in the medium are crucial for the full expression of this enterotoxic moiety, *Shigella flexneri* 2a strain M4243 was cultured in $Fe^{++}$-containing medium (L-broth) and $Fe^{++}$-depleted medium (syncase broth). After 24 and 72 hours of incubation for each medium, sterile, supernatants were obtained and then injected into ileal loops, as described above. The results are shown in Experiment 2 in Table 1 above.

As shown in Experiment 2 in Table 1 above, $Fe^{++}$-depleted culture conditions are required in order to detect expression of the enterotoxins. Further, enterotoxin expression was not notably affected by the length of incubation.

The results obtained in the rabbit ileal loop assay were compatible with elaboration of an enterotoxin by M4243.

C. Ussing Chambers

These experiments were performed as previously described by Guandalini et al, *J. Pediatr. Gastroenterol. Nutr.,* 6:953–960 (1987). Briefly, male adult New Zealand white rabbits weighing 2–3 kg were anesthetized by methoxyflurane inhalation and then sacrificed by air embolism. A 20 cm segment of distal ileum was removed, opened along the mesenteric border, rinsed free of intestinal contents, and stripped of muscular and serosal layers. Four pieces of intestine so prepared were then mounted in lucite Ussing chambers (1.12 $cm^2$ opening), and bathed in Ringer's solution containing 53 mM NaCl, 5.0 mM KCl, 30.5 mM $Na_2SO_4$, 30.5 mM mannitol, 1.69 mM $Na_2HPO_4$, 0.3 mM $NaH_2PO_4$, 1.25 mM $CaCl_2$, 1.1 mM $MgCl_2$ and 25 mM $NaHCO_3$. During the experiment, the tissue was kept at 37° C. and gassed with 95% $O_2$-5% $CO_2$. Once the tissue reached a steady-state condition, 300 µl of either M4243, M4243avir or BS103 sterile supernatants from $Fe^{++}$-depleted cultures were added to the mucosal surface, resulting in a 1:33 dilution of the original culture filtrate concentration (0.3 ml into 10 ml of Ringer's solution). 300 µl of either M4243, M4243avir or BS103 sterile supernatants were also added to the serosal side to preserve osmotic balance. Variation in transepithelial electrical potential difference (delta PD), total tissue conductance (Gt) and short-circuit current (delta Isc) were recorded. The 30–100 kDa supernatant fraction from EIEC (0136:H-), and CHELEX®-treated syncase broth (culture media) were also tested in the same manner as positive and negative controls, respectively. Four animals were employed for each test. The results are shown in FIG. 1.

As shown in FIG. 1, the overall increase in Isc was significantly greater for the M4243 supernatant as compared to the negative control (culture medium) (**=p<0.02), and similar in magnitude to that induced by the positive control (EIEC 0136:H-). On the other hand, supernatant from the plasmid-cured derivatives M4243avir and BS103 expressed significantly less enterotoxin in comparison with the plasmid-containing parent strain (*=p<0.05). However, the enterotoxic activity of the M4243avir and BS103 supernatants was nevertheless significantly greater than the negative control (culture medium) (*=p<0.05). Possible interpretations of such results include: (1) a plasmid-encoded regulation factor that regulates a chromosomal toxin gene; (2) multiple copies of the same gene located both on the *S. flexneri* 2a chromosome and the plasmid; or (3) a gene on the invasiveness plasmid encoding for a distinct enterotoxic factor. As discussed in detail below, this last hypothesis turned out to be correct.

The plasmid-cured derivative of strain M4243 showed less enterotoxic activity compared to the wild-type in both ileal loops and in Ussing chambers. Only in Ussing chambers did M4243avir induce changes that were significantly different from the negative control; this could be due to the higher sensitivity of the Ussing chamber technique as compared to the ileal loop assay. These data suggest that, while not absolutely necessary for the effect, the virulence plasmid of *Shigella flexneri* 2a M4243 enhances enterotoxic activity.

D. Enterotoxin Neutralization

EIEC (0136:H-) and *Shigella flexneri* 2a share many similarities, e.g., surface antigens, identical plasmids (pInv), clinical manifestations, etc. Thus, neutralization experiments were carried out to determine if there is any immunological relatedness between the enterotoxin produced by EIET (0136:H-) and the enterotoxins produced by M4243.

More specifically, 600 µl of the 30–100 kDa fraction of M4243 sterile supernatant (see Section E. below) were incubated for 60 min at 37° C. with 60 µl of anti-ShET polyclonal sera (anti-*Shigella flexneri* 2a enterotoxins) or with anti-EIET polyclonal sera (anti-enteroinvasive *E. coli* enterotoxin) or with pre- or post-challenged convalescent sera.

Anti-ShET polyclonal sera, anti-EIET polyclonal sera and convalescent sera were obtained as described in Example 2.

The resulting samples were tested in Ussing chambers as described in Section C. above with half of each mixture added to each side of a chamber. The results are shown in FIGS. 2A–2D.

As shown in FIGS. 2A–2D, the electrical response in Ussing chambers was drastically reduced when M4243 supernatant was pre-incubated with polyclonal rabbit antibodies raised against the *Shigella flexneri* 2a enterotoxins (anti-ShETs) or with convalescent sera from volunteers who had been challenged with *Shigella flexneri 2a.* This neutralization was not observed in either of the pre-immune sera control experiments in which responses were similar to those seen when testing the active fraction alone.

Only a partial cross-neutralization was observed when the M4243 supernatant was pre-incubated with polyclonal antibodies raised against the enteroinvasive *E. coli* enterotoxin (anti-EIET). In FIGS. 2A–2D, the number of animals tested was 4. Values are mean ±SE. *=p<0.05 and **=p<0.02 compared to PBS (the negative control).

Taken together, the above results suggest that *S. flexneri* 2a supernatant probably contains two enterotoxin moieties, ShET1 (whose gene is located on *S. flexneri* 2a chromosome) and ShET2 (whose gene is located on the invasiveness plasmid). Both enterotoxins were neutralized when anti-*S. flexneri* 2a antiserum was used. The ability of EIEC antiserum to partially neutralize the *S. flexneri* supernatant enterotoxicity was found to be due to the high similarity (at least 99% homology) of the EIET gene with the ShET2 gene (see below).

E. Estimate of Molecular Mass

To obtain an estimate of the $M_r$ of the *Shigella flexneri* 2a enterotoxins, sterile supernatant of M4243 was fractionated by ultracentrifugation through DIAFLO ultrafiltration membranes (Amicon Corp., Danvers, Mass.). YM100 (100,000-MW cutoff) and YM30 (30,000-MW cutoff) membranes were utilized to produce fractions defined by these size limits. Membrane retentates were washed free of lower molecular weight species with phosphate buffered saline (pH 7.3) (PBS), by two successive 10:1 volume dilutions with PBS, reconcentration, and final reconstitution to the original volume in PBS.

The individual fractions, representing coarse molecular weight pools of >100 kDa, 30–100 kDa and 0.5–30 kDa, were tested for enterotoxic activity in Ussing chambers and ileal loops. The results are shown in FIGS. 3A–3B.

Figure 3A:
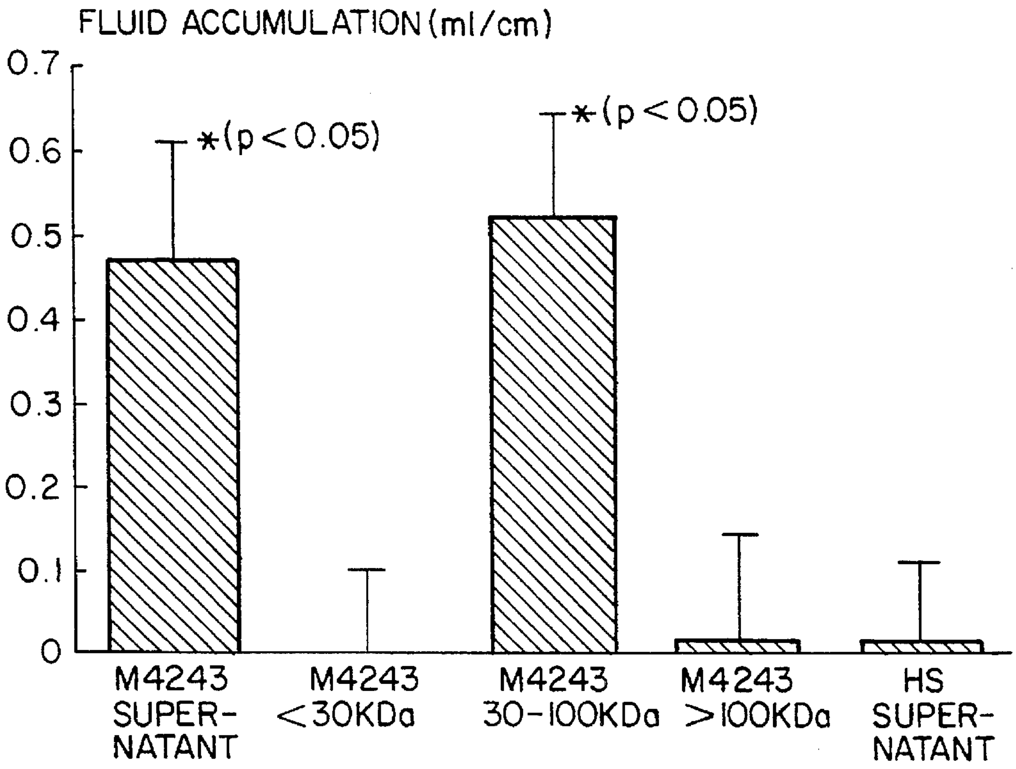
FIGS. 3A–3B show the molecular mass determination of the *Shigella flexneri* 2a strain M4243 enterotoxic moieties when assayed in rabbit ileal loops (FIG. 3A), and in Ussing chambers (FIG. 3B). In the rabbit ileal loop assays, fluid accumulations were measured and in the Ussing chambers, variations in short-circuit current (delta Isc) were measured.
Figure 3B:
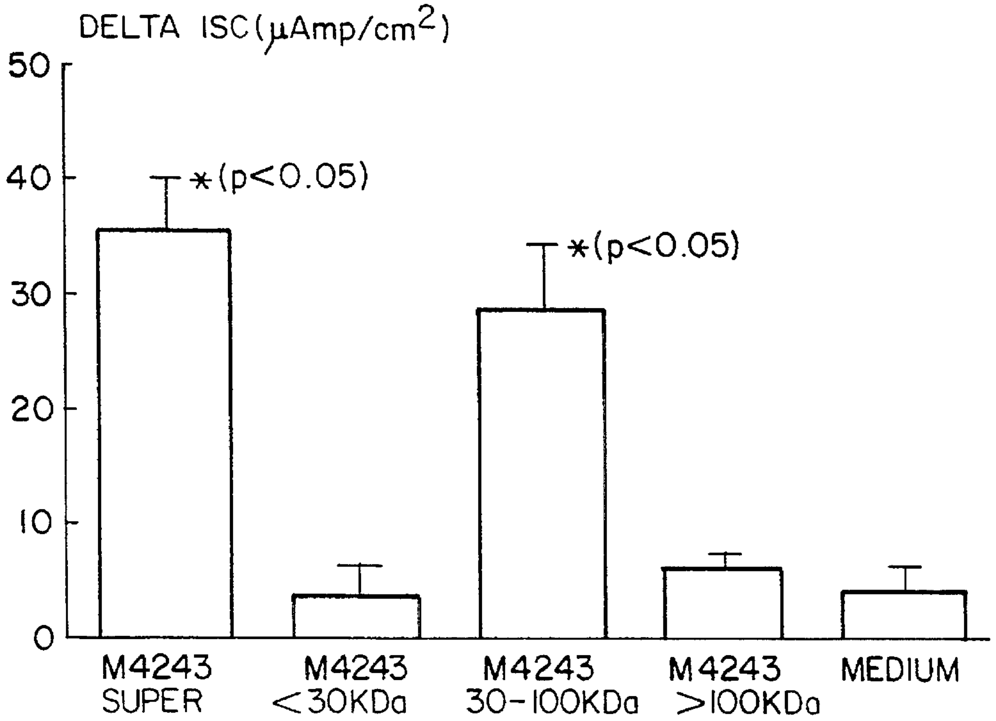

As shown in FIGS. 3A–3B, both ileal loop (FIG. 3A) and Ussing chamber (FIG. 3B) assays localized the active enterotoxic fraction within the 30–100 kDa size range. In FIGS. 3A–3B, the number of animals tested was 4. Values are means +SE. *=p<0.05 and **=p<0.02 compared to the other fractions and the negative control.

F. Cytotoxicity Assay

To establish whether there is a correlation between enterotoxic activity and cytotoxic activity, the following experiments were carried out.

A cell lysate was obtained as follows: Cultures from strain M4243 were harvested by centrifugation at 12,000 ×g for 20 minutes at 4° C. Supernatants were passed through a 0.45

μm filter, and retained for assay. The bacterial cells were then washed twice in PBS, resuspended in 1.5 ml of PBS and disrupted in a French pressure cell at 12,000 lb/in$^2$ to obtain a cell lysate (Fasano et al, *Infect. Immun.*, 58:3717–3723 (1991)). The cell lysate was then mixed with 3.5 ml of PBS (final volume 5.0 ml), clarified by centrifugation at 18,000 ×g for 20 minutes at 4° C., and filter-sterilized using a 0.45 μm membrane.

Fractions of the culture supernatant of strain M4243 were obtained as described in Section E. above.

Cytotoxicity assays were performed on the cell lysate and 3 different culture supernatant fractions (less than 30 kDa, 30–100 kDa, and more than 100 kDa), using Vero cells by the method of Gentry et al, *J. Clin. Microbiol.*, 12:361–366 (1980)). Serial two-fold dilutions (1:2 to 1:64) of the culture supernatant fractions and cell lysate were tested, and the cytotoxic dose required to kill 50% of the Vero cells (CD50) was estimated spectrophotometrically Gentry et al, *J. Clin. Microbiol.*, 2:361–366 (1980)).

Whole culture supernatants and cell lysates of enterohemorrhagic *E. coli* (EHEC) strain 933J, serotype 0157:H7, which elaborates Shiga-like toxin 1 (SLT1), were used as the positive control in the Vero cell cytotoxicity assay (Fasano et al, *Infect. Immun.*, 58:3717–3723 (1991)). The whole supernatant of non-pathogenic *E. coli* strains HS, which has been used extensively as a negative control in assays of pathogenicity and in clinical studies (Levine et al, Lancet, I:1119–1122 (1978); and Levine et al, *J. Infect. Dis.*, 148:699–709 (1983)), was used as a negative control in the Vero cell cytotoxicity assay.

Since the positive control (EHEC) killed more than 50% of the Vero cells at a 1:64 dilution, a 10-fold dilution of both supernatants and lysates from EHEC was tested. Cytotoxic titers were expressed as the reciprocal of the CD50/mg protein of the 30–100 kDa culture supernatant fraction or cell lysate; the protein content was measured by the method of Bradford, *Anal. Biochem.*, 72:248–254 (1976).

Both supernatant and lysate of the positive control strain EHEC strain 933J serotype (0157:H7) showed a high level of cytotoxicity ($0.5\times10^3$ and $3.4\times10^4$ $CD_{50}$/mg protein, respectively). In contrast, the supernatant of HS, the negative control, showed no cytotoxic activity. Against these two extremes, M4243 exhibited a low-level of cytotoxic activity which was restricted to the less than 30 kDa supernatant fraction ($4.2\times10^2$ CD50/mg protein) and the cell lysate ($5.1\times10^2$ $CD_{50}$/mg protein).

The cytotoxic assay described above was repeated, except that HeLa cells were substituted for Vero cells. As a result of this experiment, it was determined that the 30–100 kDa fraction obtained from *Shigella flexneri* 2a supernatant and cell lysate also does not possess any cytotoxic activity against HeLa cells. On the other hand, as expected, and consistent with the results obtained using Vero cells, only the less than 30 kDa supernatant fraction obtained from *Shigella flexneri* 2a possesses cytotoxic activity against HeLa cells ($3.2\times10^2$ $CD_{50}$/mg protein). Also as expected, the cell lysate fraction from *Shigella flexneri* 2a, which contains the less than 30 kDa fraction possesses cytotoxic activity against HeLa cells ($4.4\times10^2$ $CD_{50}$/mg protein).

Thus, the enterotoxin (30–100 kDa fraction) activity and cytotoxin (less than 30 kDa fraction) activity found in *Shigella flexneri* 2a are the result of two distinct moieties.

Hence, the enterotoxins appear to be responsible for the diarrhea induced by *Shigella flexneri* 2a, since the 30–100 kDa fraction (where the enterotoxic activity was localized) was responsible for fluid accumulation in rabbit ileal loops and in electrical responses in Ussing chambers.

EXAMPLE 2

Preparation of Antitoxin

A. Preparation of Antibodies in Rabbits 1.0 ml of the 30–100 kDa fraction from the supernatant of *Shigella flexneri* 2a strain M4243 that showed enterotoxic activity was mixed with an equal volume of Freund's complete adjuvant and inoculated intramuscularly in four separate sites in male New Zealand white rabbits. A booster dose (1.0 ml) was administered four weeks later, and one month thereafter the animals were bled to obtain antisera. Antisera to EIEC enterotoxin (EIET) from strain CVD/EI-34 (0136:H-) was prepared in the identical manner. These antisera are herein referred to as anti-*Shigella flexneri* 2a enterotoxins (anti-ShETs), and anti-enteroinvasive *E. coli* enterotoxin (anti-EIET).

B. Preparation of Antibodies in Humans

Figure 4:
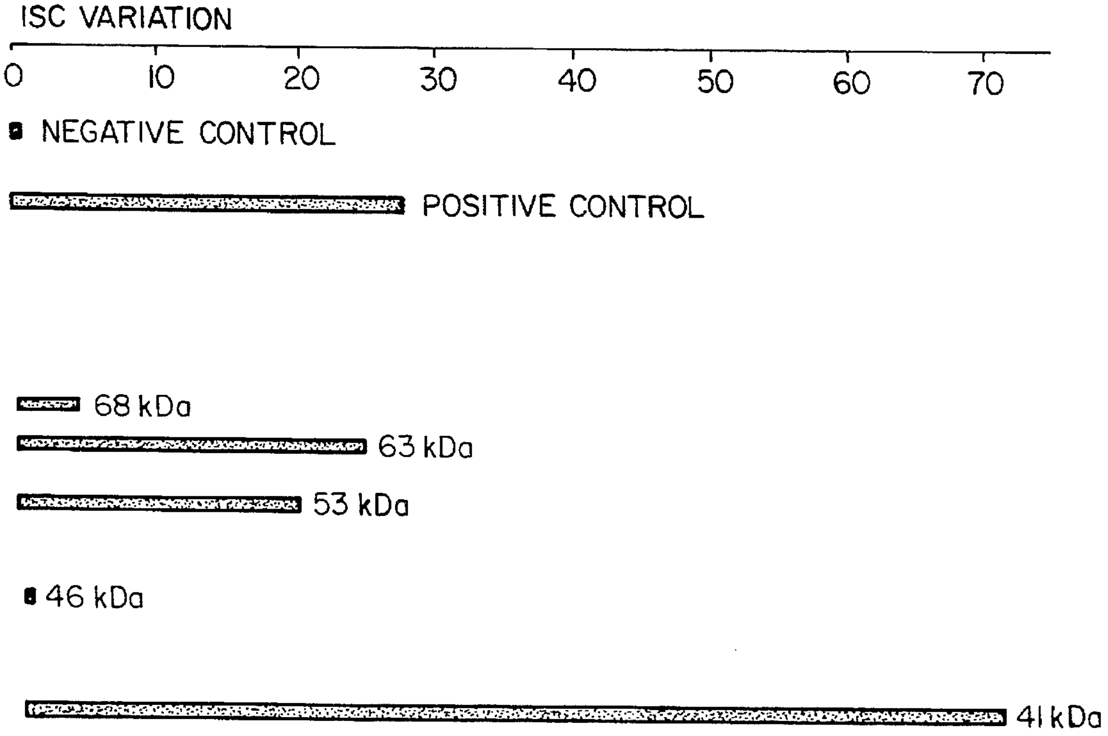
FIG. 4 shows the results of assays for enterotoxic activity in Ussing chambers when using protein bands from SDS-PAGE obtained from strain M4243avir (containing only ShET1 enterotoxin) that represent the 65–75 kDa column fraction, an extract of an unused strip of nitrocellulose (negative control), and a sample representing the 65–75 kDa column fraction (positive control). Values are given as Isc variation ($\mu Amp/cm^2$).
Figure 2A:
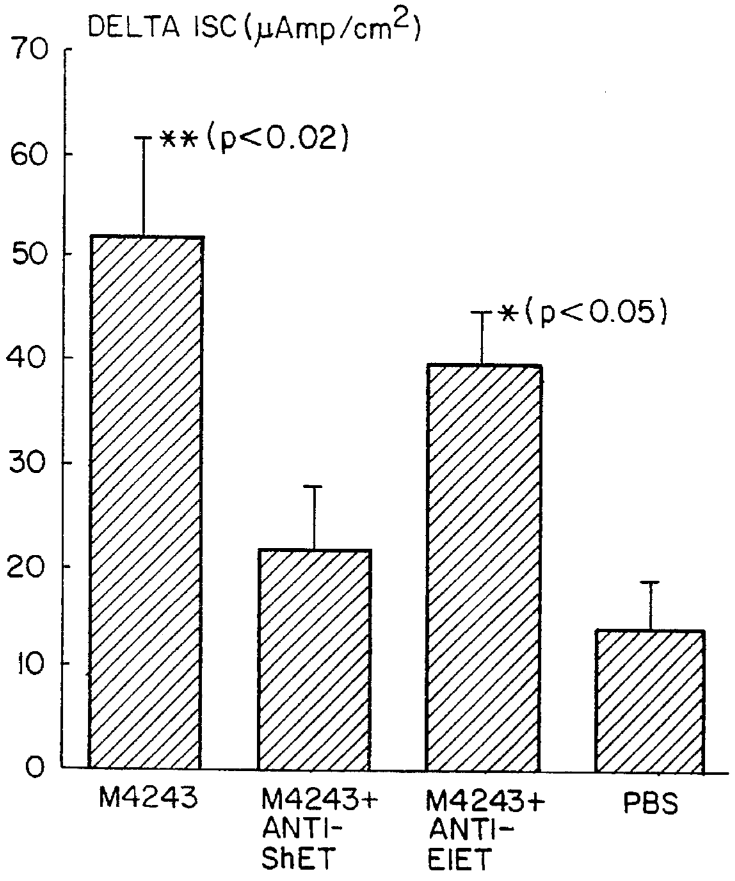
FIG. 2 shows the results of assays for enterotoxic activity in Ussing chambers when using *Shigella flexneri* 2a strain M4243 culture supernatant which was first neutralized with anti-sera against the *Shigella flexneri* 2a enterotoxins (anti-ShETs), with anti-sera against the EIEC enterotoxin (anti-EIET), with pre-challenge sera or post-challenge sera of volunteers challenged with wild-type *Shigella flexneri 2a.* In these assays, variations in short-circuit current (delta Isc) (FIGS. 2A and 2C), and transepithelial electrical potential differences (delta PD) (FIGS. 2B and 2D) were measured.
Figure 2B:
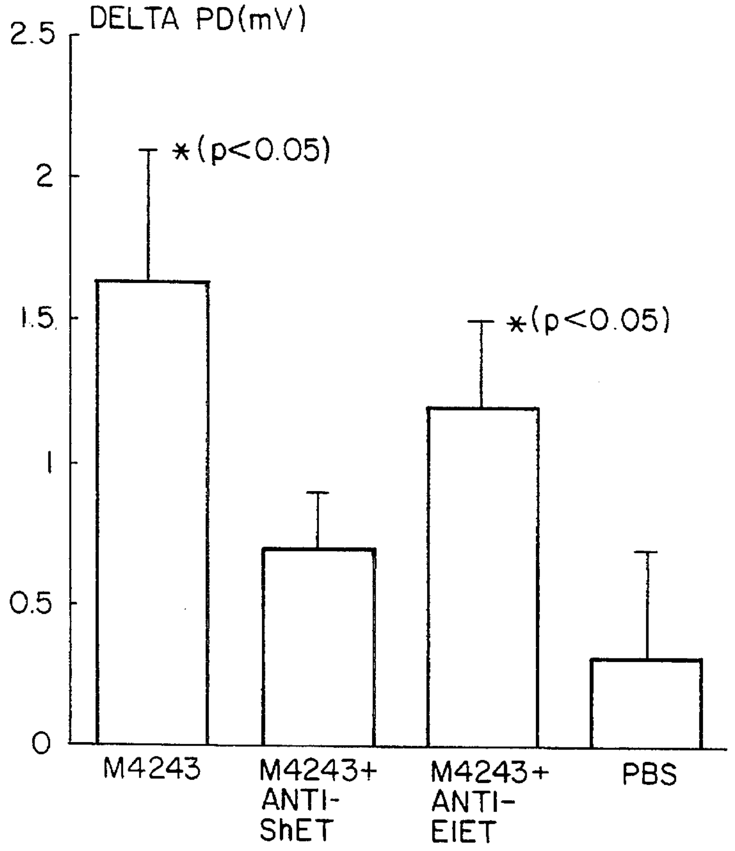
Figure 2C:
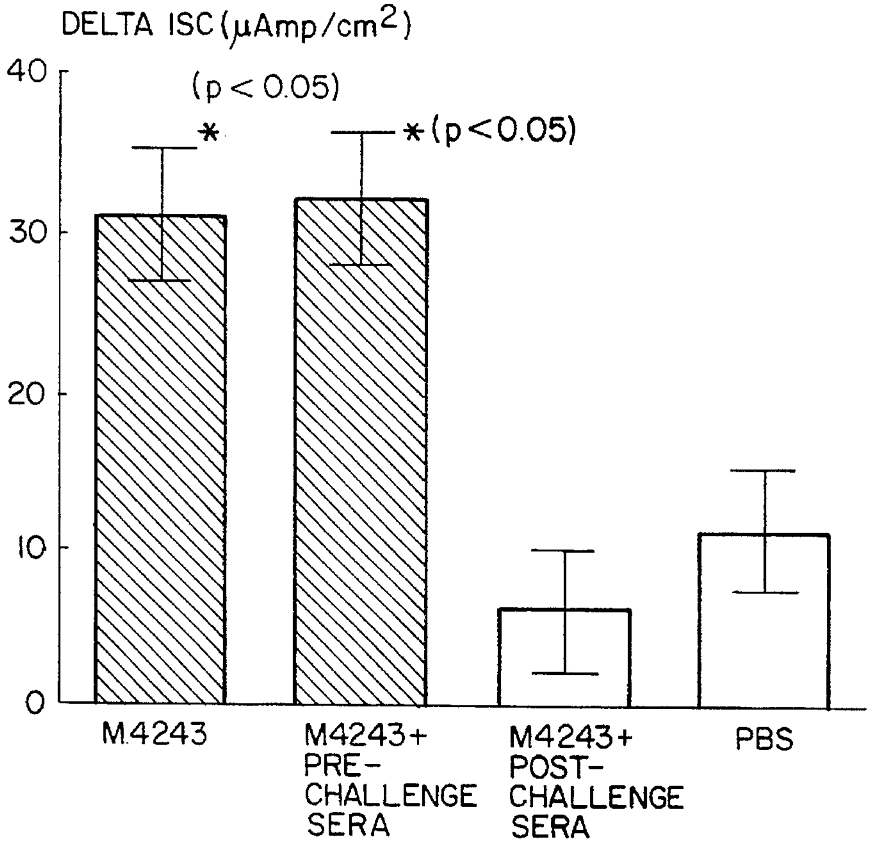
Figure 2D:
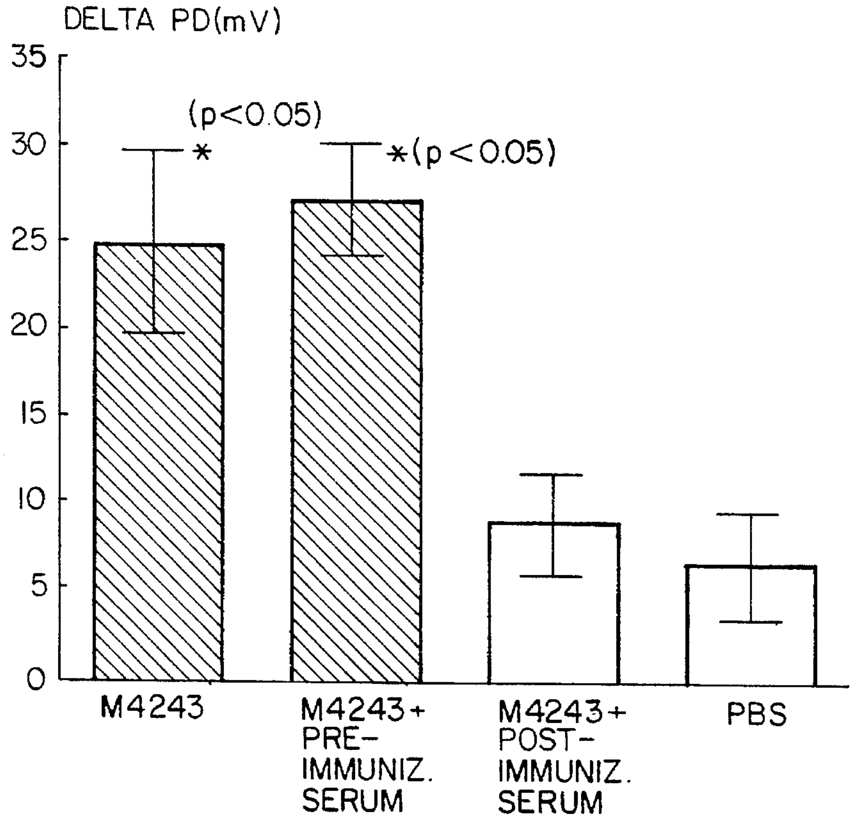

Pre- and post-challenged (convalescent) serum pools from 10 adult volunteers who developed diarrhea after ingesting *Shigella flexneri* 2a M4243 (Kotloff et al, *Infect. Immun.* 60:2218–2224 (1992)) were prepared for use in neutralization experiments in Ussing chambers (FIGS. 2C and 2D), and for Western immunoblots (FIG. 4).

EXAMPLE 3

Purification and Partial Sequencing of Shigella Enterotoxin 1 (ShET1)

A. Purification

Large-scale preparation of *Shigella flexneri* 2a enterotoxin was undertaken in order to obtain sufficient material for further characterization and analyses. Plasmid-cured *S. flexneri* 2a M4243avir was used in order to avoid expression of both ShET2 and plasmid-encoded membrane associated proteins (Hale et al, *Infect. Immun.*, 50:620–629 1985)), which are known to be similar in size to the fractions exhibiting enterotoxic activity and to be antigenic in volunteers (Van De Verg et al, *J. Infect. Dis.*, 66:158–161 (1992)).

More specifically, plasmid-cured *Shigella flexneri* 2a was inoculated into 30 liters of L-broth containing 25 μg/ml of the iron-chelator, ethylenediamine-N-N'-diacetic acid (EDDA) (Rogers, *Infect. Immun.*, 7:445–456 (1973)), and incubated overnight at 37° C. in the New Brunswick Scientific 30 liter fermentor. Bacterial cells were removed by centrifugation at 5,000 ×g in a Sharples industrial centrifuge, and the supernatant was filtered through a 0.45 μm filter. This filtrate (approximately 30 liters) was fractionated to isolate and concentrate 100-fold the moieties falling within the 30–100 kDa range as described above, except Pellicon tangential flow cassettes (Millipore) were used for ultrafiltration processing of these larger volumes. This filtrate exhibited enterotoxic activity similar to levels observed for smaller batches employing the plasmid-cured strain.

A 10 ml aliquot of the 30–100 kDa concentrate was then further fractionated by replicate separations with an HPLC size exclusion column (SEC-2000, 7.5×600 cm with guard column, Phenomenex, Torrance, Calif.). Fractions were eluted from the column with PBS at 0.5 ml/min. The fractions containing moieties in the 65–75 kDa range were collected, pooled and concentrated by vacuum dialysis to 1.0 ml employing a 10 kDa membrane (MicroProDiCon, Spectrum Medical Industries, Los Angeles, Calif.). An aliquot of this material was reserved for enterotoxin assay, and the remainder was separated by sodium dodecyl sulfate polyacrylamide gel electrophoresis (SDS-PAGE) (Laemmli, *Nature,* 227:680–685 (1970)) using an 11 cm preparative well with peripheral marker lanes. The resultant 18 bands were transferred to a nitrocellulose membrane by the method of Towbin et al, (Towbin et al, *Proc. Natl. Acad. Sci.* U.S.A., 76:4350–4354 (1979)). Multiple 2 mm wide vertical strips of the nitrocellulose membrane were prepared and stained with colloidal gold (Aurodye, Janssen Pharmaceutical, Piscataway, N.J.) to visualize protein bands, or reacted with the pooled convalescent sera from humans challenged with *Shigella flexneri* 2a M4243 by Western immunoblotting techniques (Vial et al, *J. Infect. Dis.,* 158:70–79 (1988)).

Five protein bands were identified by the convalescent serum Western strips indicating their antigenic relatedness. The five protein bands were aligned with the remainder of the nitrocellulose blot which had been reversibly stained with Ponceau S (colloidal gold (Harlow et al, *Antibodies: A Laboratory Manual,* p. 494 (1988)). Using a scalpel, bands of about 10 cm in length corresponding to immunoreactive that ShET1 is expressed in vivo where it elicits an immune response. Thus, it is likely that this enterotoxin plays a role in the pathogenesis of Shigella diarrhea in humans.

B. N-terminal Sequencing of ShET1

To obtain greater protein mass for sequencing, scale-up of the chromatographic procedure was preformed using Sephacryl S-200 (Pharmacia, Piscataway, N.J.) packed in a calibrated, 4° C. jacketed, 5×100 cm XK 50/100 column (Pharmacia). The 65–75 kDa size fraction was handled as above except that a polyvinylidine diflouridine membrane (Immobilon, Millipore), was substituted for nitrocellulose for electrophoretic transfer. The three protein bands, identified as described above, were excised, extensively rinsed with distilled water and dried. Individual strips bearing the protein bands were then subjected to N-terminal sequencing on an Applied Biosystems model 477A sequencer, as described by Hall et al, *J. Bacteriol.,* 171:6372–6374 (1989). The determined N-terminal sequence data are shown in Table 2 below.

TABLE 2

Preliminary N-terminal amino acid sequence of Shigella enterotoxin 1

| MW of entero-toxic moiety | Proposed A:B subunit ratio• | N-terminal amino acid sequence 1‡ | 2 | 3 | 4 | 5 | 6 | 7 | 8 | 9 | 10 | 11 | 12 | 13 | 14 |
|---|---|---|---|---|---|---|---|---|---|---|---|---|---|---|---|
| 63 kDa | A1:B3 | Ala | Pro | Pro | Val (SEQ ID NO:3) | | | | | | | | | | |
| | | Asp§ | Thr | | Leu | | | | | | | | | | |
| 53 kDa | A1:B2 | Ala | Pro | Pro | Val (SEQ ID NO:3) | | | | | | | | | | |
| | | Asp | Thr | | Leu | | | | | | | | | | |
| 41 kDa | A1:B1 | Ala | Pro | Pro | Val | Pro | Ile | Asn | Pro | Ala | Xaa | Pro | Ile | Xaa | Arg* |
| | | Asp | Thr | | | Glu | | | | Phe | | Arg | Arg | | |

•assuming an A subunit size of about 30 kDa and a B subunit size of about 11 kDa
‡sequencing cycle number
§Duplicate amino acid signals detected for samples at positions indicated
*(SEQ ID NO:4)

material from each of the five protein bands were carefully excised by identification and alignment with the Western and protein stained strips. Material from each of these bands were eluted (Montelero, *Electrophoresis,* 8:432–438 (1987)) by dissolution of the nitrocellulose in 200 μl of dimethyl sulfoxide, addition of four volumes of water to precipitate the nitrocellulose, followed by centrifugation at 10,000 ×g, and dialysis of the supernatant against PBS.

Each sample, in addition to the reserved 65–75 kDa sizing column fraction, and material from a mock-blotted and extracted nitrocellulose strip as positive and negative controls, respectively, was then tested for enterotoxic activity in Ussing chambers, as discussed in Example 1 above. The results are shown in FIG. 4.

As shown in FIG. 4, three of the bands, of approximate MW 63 kDa, 53 kDa and 41 kDa, exhibited enterotoxic activity. Replicates of a band corresponding to a MW of 41 kDa showed a consistent mean rise in Isc of 70.4 Amp/cm$^2$, whereas the 63 kDa and 53 kDa bands exhibited rises in Isc of 24.3 and 19.5 Amp/cm$^2$, respectively The remaining two immunoreactive bands showed no enterotoxic activity.

The observation that convalescent sera from volunteers who were fed wild-type *S. flexneri* 2a contain antibodies that neutralize the enterotoxic activity *S. flexneri* 2a supernatants in Ussing chambers, and that specifically bind to immobilized protein shown to produce such activity, demonstrates As shown in Table 2 above, a definitive extended sequence could not be determined from the material available for any of the three bands. However, the identical putative amino acid sequence was found for the first four residues of all three bands. Moreover, the data derived suggested that two distinct N-termini were being identified. Notably, this was consistent for all three bands examined.

The University of Wisconsin package (Genetics Computer Group, Madison, Wis.) (Devereux et al, *Nucleic Acids Res.,* 12:387–395 (1984)), data bases containing known protein sequences and untranslated DNA sequences were perused to identify those with potential amino acid homology to the putative N-terminal sequences acquired from the above samples. GenBank release 75.0 and PIR Protein 35.0 were also examined using the TFASTA and WORDSEARCH programs. No apparent regions of extensive alignment were found to exist. In addition, no substantial homology to known bacterial toxins was detected.

The common A:$B_n$ active:binding unit motif frequently encountered in bacterial enterotoxins, including cholera toxin (CT) (LoSpalluto et al, *Biochem. Biophys. Acta,* 257:158–166 (1972)), heat-labile enterotoxin (LT) of enterotoxigenic *E. coli* (Clements et al, *Infect. Immun.,* 38:806–809 (1982)) and Shiga toxin of *S. dysenteriae* 1 (Olsnes et al, *J. Biol. Chem.,* 256:8732–8738 (1981); and Seidah et al, *J. Biol. Chem.,* 261:13928–13931 (1986)), may be reflected in the above data. That is, as proposed in Table 2, the apparent molecular sizes of active material are consistent with such stoichiometries based upon the sizes of the A (28–32 kDa) and B (7.7–11 kDa) subunits of the previously identified enterotoxins. By extension, a holotoxin consistent with a size of 65–75 kDa and an A1:B4 structure would be predicted by these conventions. These tentative configurations also satisfy the usual requirements for both a binding and an active domain that allow the enterotoxin to attach and gain entrance to enterocytes and to initiate events that culminate in intestinal secretion.

EXAMPLE 4

Gene sequencing of Enteroinvasive *E. coli* Enterotoxin

A genetic approach was employed to identify and clone the enterotoxin from enteroinvasive *E. coli.* More specifically, TnphoA insertion mutants were generated in EIEC strain EI-37 (0136:NM) (Fasano et al, *Infect. Immun.*, 58:3717–3723 (1991)) as described by Taylor et al, *J. Bacteriol.*, 171:1870–1978 (1989). The resulting TnphoA insertion mutants were screened for increased expression of alkaline phosphatase in low iron L-agar (containing 30 μg/ml of EDDA) compared with standard L-agar. As a result, nine insertion mutants with increased expression of alkaline phosphatase were identified.

The supernatants from the resulting nine TnphoA insertion mutants were then tested in Ussing chambers as described above, and two of the mutants were found to have significantly less enterotoxic activity, as defined by changes in $I_{sc}$, than the wild-type parent, suggesting that the phoA gene was inserted into the open reading frame that encodes enterotoxic activity.

Figure 5:
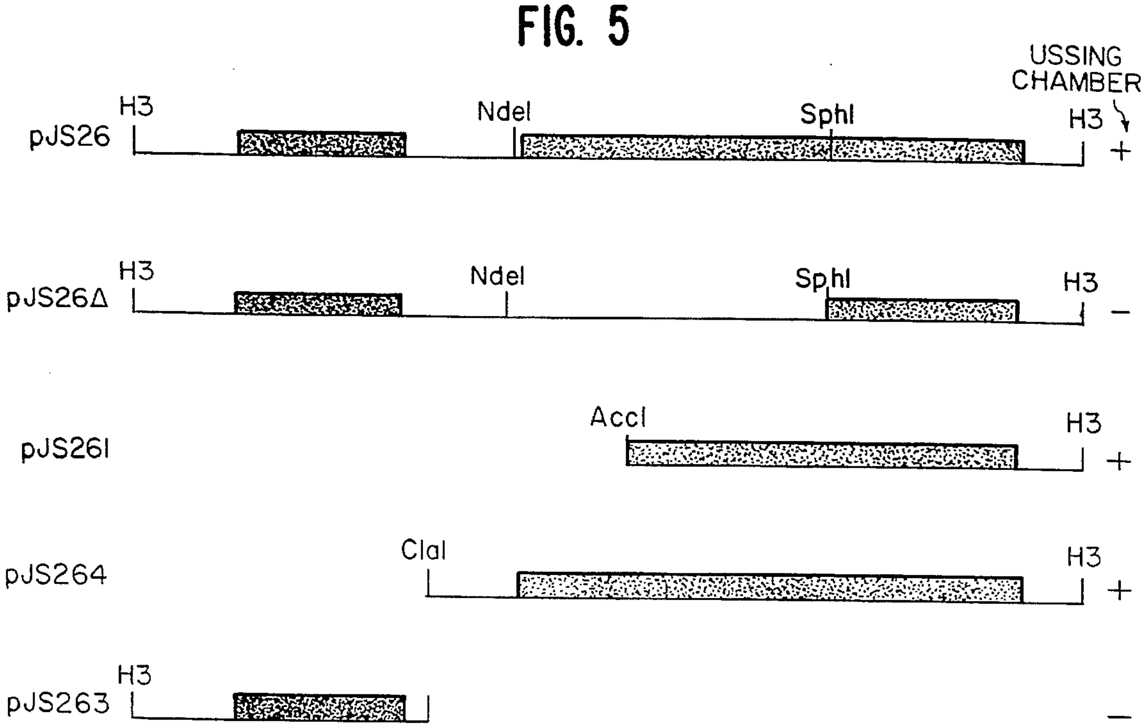
FIG. 5 shows a restriction map for the fragment in pJS26 which contains the tie gene, as well as restriction maps for the relevant portions of plasmids derived from pJS26.

DNA was then purified from the two mutants, and the purified DNA was digested with BamHI. The resulting DNA fragments, which flank the TnphoA insertions, were cloned into the BamHI site of vector pBluescript Sk/± (Stratagene, La Jolla, Calif.). Then, the cloned DNA was hybridized against a pHC79 cosmid library of EIEC strain EI-34 (Fasano et al, *Infect. Immun.*, 58:3717–3723 (1991)). The flanking DNA sequences from one of the two TnphoA insertion mutants were found to be homologous to nine cosmid clones. Random subcloning of these cosmid clones into pBluescript Sk/± led to the identification of a 2.8 kb HindIII fragment which was found to encode enterotoxin activity in Ussing chambers. This fragment, when cloned into the HindIII site of pBluescript Sk/±, gave rise to pJS26 (FIG. 5). DH5α (Gibco/BRL Life Technologies, Gaithersberg, Md.) was transformed with pJS26, and found to confer reproducible increases in Isc in Ussing chambers.

The 2.8 kb HindIII fragment was manually sequenced, and two potential open reading frames (orf's), encoding predicted peptides of 62.8 kDa and 16.1 kDa were found (FIG. 5).

The 2.8 kb HindIII fragment was digested with ClaI and subcloned into HindIII- and ClaI-digested pBluescript Sk/±, to give rise to pJS264, which contained only the 62.8 kDa orf (FIG. 5). DH5α transformed with pJS264 exhibited rises in Isc in Ussing chambers similar to that found with the entire 2.8 kb HindIII fragment. This orf, whose DNA sequence, along with the determined amino acid sequence are shown in FIGS. 6A–6C (SEQ ID NO:1), was therefore designated tie (for "toxin invasive *E. coli*").

The 2.8 kb HindIII fragment was also digested with ClaI and subcloned into HindIII- and ClaI-digested pBluescript Sk/±, to give rise to pJS263, which contained only the 16.1 kDa orf (FIG. 5). DH5α transformed with pJS264 did not elicit rises in Isc in Ussing chambers.

A GenBank search for amino acid homology of the translated orf's revealed no significant identity to any known prokaryotic sequences.

The 2.8 kb HindIII fragment containing the tie gene was then digested with AccI and cloned into DH5α so as to obtain pJS261 (FIG. 5), which was then used to transform DH5α. The resulting transformant was also found to express enterotoxic activity when tested in Ussing chambers as described above.

In order to gauge the effect of the tie gene on secretory activity, a deletion mutation was constructed by digesting the tie gene in pJS26 with 10NdeI and SphI. The resulting plasmid was designated pJS26a (FIG. 5). This plasmid lacked the first two-thirds of the N-terminus of the open reading frame. This plasmid was then used to transform DH5α, and tested in Ussing chambers as described above. The supernatant obtained from the pJS26a transformants elicited less response in the Ussing chamber assay when compared to pJS26, confirming that tie gene is the EIET structural gene.

Thus, unlike ShET1, which as discussed above is believed to be composed of A and B subunits, EIET is a single molecule.

EXAMPLE 5

Gene sequencing of Shigella enterotoxin 2 (ShET2)

As discussed above, Shigella and EIEC share some similarities. Thus, the orf containing the gene encoding the EIEC enterotoxin shown in FIGS. 6A–6C (SEQ ID NO:1) was used as a probe to determine whether Shigella has similar DNA sequences.

More specifically, purified genomic DNA was obtained from each of *S. flexneri* 2a M4243 and *S. flexneri* 2a M4243avir, digested with SalI, and then screened for hybridization with the tie gene. The DNA—DNA hybridization showed the presence of a single 3.5 kb band in genomic DNA from the wild-type strain, but not from the plasmid-cured derivative. This result suggests that the homologous DNA is located on the invasiveness plasmid.

The 3.5 kb SalI fragment was identified on the *S. flexneri* 2a M4243 plasmid by PCR using the following oligonucleotide primers that hybridize to the tie gene (CAGTGTATCACCACGAG (SEQ ID NO:13); and AAATTATCTACAGTCAG (SEQ ID NO:14)), and sequenced using an automated sequencer. The resulting DNA sequence, along with the determined amino acid sequence are shown in FIGS. 7A–7C (SEQ ID NO:2). As shown in FIGS. 7A–7C (SEQ ID NO:2), this fragment was found to contain a 1595 bp open reading frame and has at least 99% homology to the EIET gene. This Shigella gene encodes for a protein of a predicted MW of 63 kDa, and a pI of 6.36. No leader peptide was identified. The analysis of the peptide structure revealed three possible membrane spanning domains (amino acid positions 120–140, 260–300 and 480–520) and five cysteine residues. A predicted ribosome binding site is found at nucleotide positions 290–293. When the translation of this open reading frame was compared to the N-terminal sequence of ShET1 shown in Table 2, no homologies were found, suggesting that this gene, located on the *S. flexneri* 2a M4243 plasmid, encodes for a toxin (hereinafter named "ShET2") which is distinct from ShET1, but substantially identical to EIET.

Due to the similarity between the EIET gene and the ShET2 gene, it is evident that the gene located on *S. flexneri* 2a M4243 plasmid, i.e., that hybridized with EIET gene probe, is the ShET2 structural gene.

EXAMPLE 6

Use of EIEC enterotoxin gene as a DNA probe

The tie gene was used as a DNA probe, and hybridized against a collection of EIEC and Shigella strains under high stringency by the standard colony blot method. The results are shown in Table 3 below.

TABLE 3

Prevalence of tie Gene in *E. coli* and Shigella Colony Blot Hybridization with tie Probe

| Category | Positive | Negative | % Positive |
|---|---|---|---|
| Shigella | 27 | 7 | 80% |
| EIEC | 60 | 20 | 75% |
| Other *E. coli* | 0 | 110 | 0% |

As shown in Table 3 above, tie-homologous sequences are present in 80% (27/34) of Shigella strains, including members of all four Shigella species (flexneri, boydii, sonnei and dysenteriae), and 75% of EIEC. None of 110 *E. coli* tested, other than EIEC, carried homologous sequences.

EXAMPLE 7

Construction of the attenuated *S. flexneri* 2a strain CVD1202

*S. flexneri* 2a strain 2457T (Kotloff et al, *Infect. Immun.* 60:2218–2224 (1992)), known to be virulent based on experimental challenge studies in adult volunteers, was selected as the wild-type parent to be attenuated by introduction of a deletion in both the aroA and VirG genes.

More specifically, the aroA gene (Duncan et al, *FEBS,* 170:59–63 (1984)) was subjected to polymerase chain reactions in a Programmable Thermal Controller unit, using Tag polymerase and buffer obtained from Promega to obtain a deletion of 201 nucleotides in the aroA gene, which corresponds to a deletion of amino acids 168–231 of the encoded enzyme. In particular, the 5' end of the aroA gene was amplified with the upstream primer (TAATCGAATTCATG-GAATCCCTGACGTTA) (SEQ ID NO:5) so as to introduce an EcoRI site, and with the downstream primer (GGTAC-CCCCAATATTAGGGCCATCAACGT-CAACGTTGCCGCC) (SEQ ID NO:6) so as to introduce KpnI and SspI sites. The 3' end of the aroA gene was amplified with the upstream primer (AATATTGGGGGTAC-CGGTACTTATTTGGTCGAAGGCGATGCA) (SEQ ID NO:7) so as to introduce SspI and KpnI sites, and with the downstream primer (TGATAAGTCGACTCAGGCTGC-CTGGCTAAT) (SEQ ID NO:8) so as to introduce a SalI site. Both segments were amplified for 30 cycles of 1 min at 94° C., 2 min at 50° C. and 4 min at 72° C.

In a second PCR reaction, the 5' and 3' segments were fused, and the resulting fusion product was amplified in the same reaction. To facilitate this fusion, the first 15 cycles had an annealing temperature slope (1° C./8 sec from 40° C. to 50° C.+ 50° C. for 2 min), followed by 15 cycles with an annealing temperature of 55° C. in which the new ΔaroA gene was amplified. The aroA gene of Shigella was cloned into the EcoRI and SalI sites of the suicide plasmid pKTN701 (Hone et al, *Vaccine,* 9:810–816 (1991)) giving rise to suicide vector pShΔaroA2, which was propagated in strain SY327 (Miller et al, *J. Bactiol.,* 170:2575–2583 (1988)). The plasmid was electroporated into strain Sm10λpir (Miller et al, *J. Bactiol.,* 170:2575–2583 (1988)). Sm10λpir(pShΔaroA2) was used to conjugate the deletion cassete into strain 2457T.

Suicide vector pShΔroA was integrated into the chromosome of strain 2457T to introduce the ΔaroA mutation by homologous recombination, followed by tetracycline-sensitive enrichment using the procedures described for Salmonella by Hone et al, *Vaccine,* 810–816 (1991).

To screen for ΔaroA mutants in which the aromatic amino acid biosynthesis pathway was inactivated, individual colonies, were grown overnight in Brain heart infusion (BHI) (BBL, Becton Dickinson, Cockeysville, MD) agar, and after carrying out the antibiotic-sensitive enrichment procedure, were inoculated onto replica plates containing Shigella minimum medium (SMM) consisting of 0.4 g NaCl, 8.4 g $K_2HPO_4$, 3.6 g $KH_2PO_4$, 0.8 g $(NH_4)_2SO_4$, 2.5 g glucose, 0.05 g nicotonic acid, 0.05 g aspartic acid, 0.05 g serine and 15 g noble L-agar. SMM allows one to screen for ΔaroA mutants colonies that cannot synthesize aromatic compounds de novo, and thus require exogenous aromatic compounds in order to grow. In this manner, the aroA strain, CVD1201, was obtained.

A deletion of 900 nucleotides in the virG gene (Lett et al, *J. Bacteriol.,* 172:352–359 (1989)), which corresponds to a deletion of amino acids 341–640 of the 120 kDA VirG protein, was obtained by following steps analogous to that used for preparing the aroA mutation. More specifically, the 5' end of the virG gene was amplified with the upstream primer (GGGGAATTCCAAATTCACAAATTTTTTTGT) (SEQ ID NO:9) so as to introduce an EcoRI site, and with the downstream primer (TCCATGCCATTCATGGAGTAT-TAATGAATT) (SEQ ID NO:10). The 3' end of the virG gene was amplified with the upstream primer (CTCCAT-GAATGGCATGGAAAGGCGGAATA) (SEQ ID NO: 11), and the downstream primer (CGGGTCGACTCAGAAGG-TATATTTCACACCCAA) (SEQ ID NO:12) so as to introduce a SalI site. Amplification and fusion of the virG 5' and 3' segments were performed using the same PCR cycles described above. The resulting new ΔvirG gene was cloned into the EcoRI and SalI sites of pKTN701, giving rise to pShΔvirG, which was propagated in strain SY327. Next, the chloramphenicol resistance gene in pShΔvirG amplified from pBR322, was replaced with the tetracycline resistance gene in plasmid pBR322 to give rise to the suicide vector pShΔvirG$^T$, which was propagated in strain SY327. The plasmid was then electroporated into strain Sm10pir. Sm10λpir(pShΔvirG$^T$) was used to conjugate the deletion cassete into the ΔaroA strain, CVD1201.

Suicide vector pShΔvirGwas then integrated into the virulence plasmid (ΔvirG) loci of the ΔaroA strain, CVD1201, to introduce the ΔvirG mutation by homologous recombination, followed by chloramphenicol-sensitive enrichment using the procedures described for Salmonella by Hone et al, *Vaccine,* 9:810–816 (1991).

The presence of the 140 MD virulence plasmid was assessed by uptake of Congo red dye by the resulting ΔaroA mutants when grown on 0.01% (w/v) Congo red dye (Sigma, St Louis, Mo.) tryptic soy agar (CR) (BBL) plates in the presence of 20 μg chloramphenicol/ml of BHI agar.

In addition, to screen for ΔvirG mutants, individual colonies were grown overnight on BHI medium, and then plated in replicate on CR and BHI in the presence of 16 μg/ml of tetracycline (Sigma).

Five-six colonies of every clone that was found to be chloramphenicol sensitive and Congo red positive, and that showed aromatic compound auxotrophy, were boiled in 100 μl of sterile water for 10 min. The resulting supernatant was used as the template for PCR screening of ΔaroA using the aroA primers shown above. In addition, five-six colonies of every clone that was tetracycline sensitive and Congo red positive were boiled in 100 μl of sterile water for 10 min. The resulting supernatant was used as the template for PCR screening of VirG using the VirG 5' and 3' upstream primers.

In this manner the aroA VirG Shigella flexneri 2a mutant, CVD1202 (ATCC No. 55517), was isolated.

While the invention has been described in detail, and with reference to specific embodiments thereof, it will be apparent to one of ordinary skill in the art that various changes and modifications can be made therein without departing from the spirit and scope thereof.

What is claimed is:

1. An isolated DNA molecule encoding ShET2 which consists of the amino acid sequence encoded by the DNA of SEQ ID NO:2.

2. The isolated DNA molecule of claim 1, wherein said DNA molecule consists of the nucleotide sequence shown in SEQ ID NO:2.

3. A plasmid comprising the DNA of claim 1.

4. A plasmid comprising the DNA of claim 2.

* * * * *

UNITED STATES PATENT AND TRADEMARK OFFICE

CERTIFICATE OF CORRECTION

PATENT NO. : 5,468,639 
APPLICATION NO. : 08/160317
DATED : November 21, 1995
INVENTOR(S) : Alessio Fasano et al.

It is certified that error appears in the above-identified patent and that said Letters Patent is hereby corrected as shown below:

Insert at Column 1, line 10 the heading --STATEMENT REGARDING FEDERALLY SPONSORED RESEARCH OR DEVELOPMENT--

Insert at Column 1, following the above heading --This invention was made with government support under NIH Grant No. AI019716 awarded by the National Institutes of Health. The government has certain rights in the invention.--

Signed and Sealed this

Twenty-fifth Day of March, 2008

JON W. DUDAS
*Director of the United States Patent and Trademark Office*

SEQUENCE LISTING ( 1 ) GENERAL INFORMATION:

( i i i ) NUMBER OF SEQUENCES: 14

( 2 ) INFORMATION FOR SEQ ID NO:1:

( i ) SEQUENCE CHARACTERISTICS:
( A ) LENGTH: 2008 base pairs
( B ) TYPE: nucleic acid
( C ) STRANDEDNESS: single
( D ) TOPOLOGY: linear ( i i ) MOLECULE TYPE: genomic DNA ( i i i ) HYPOTHETICAL: NO ( i v ) ANTI-SENSE: NO ( v i ) ORIGINAL SOURCE:
( A ) ORGANISM: Enteroinvasive E. coli
( B ) STRAIN: EI-37 (0136:NM)

( x i ) SEQUENCE DESCRIPTION: SEQ ID NO:1:

ATCGATATAT TGTTTATTGT CAGTATGGCT CAATGTGATA ATAGTTGGAA AGTTTGATGG 60

GTTTCGCCCC GTTGTAGCGG TAGTCGACCC CGTTGTAGCG GTAGTCGAGC TGGAAGGTCT 120

TCAGGCACTG CTTACAGCGA TAGAGCAGCC CCCCAGAACT GGAATGGCCG TTCCGATACC 180

CCCCTGAGTT TCAGAGTAAC GGGGACAAAC CACATCAATC TTTGCCATCA ATCATCCAAA 240

GGGCAAAGAG TACAACAACA CTAAGTCTGC GTCACAACCC ATCAATGAAA GGAATATATA 300

CAT ATG CCA TCA GTA AAT TTA ATC CCA TCA AGG AAA ATA TGT TTG CAA 348
Met Pro Ser Val Asn Leu Ile Pro Ser Arg Lys Ile Cys Leu Gln
1 5 10 15

AAT ATG ATA AAT AAA GAC AAC GTC TCT GTT GAG ACA ATC CAG TCT CTA 396
Asn Met Ile Asn Lys Asp Asn Val Ser Val Glu Thr Ile Gln Ser Leu
20 25 30

TTG CAC TCA AAA CAA TTG CCA TAT TTT TCT GAC AAG AGG AGT TTT TTA 444
Leu His Ser Lys Gln Leu Pro Tyr Phe Ser Asp Lys Arg Ser Phe Leu
35 40 45

TTA AAT CTA AAT TGC CAA GTT ACC GAT CAC TCT GGA AGA CTT ATT GTC 492
Leu Asn Leu Asn Cys Gln Val Thr Asp His Ser Gly Arg Leu Ile Val
50 55 60

TGT CGA CAT TTA GCT TCC TAC TGG ATA GCA CAG TTT AAC AAA AGT AGT 540
Cys Arg His Leu Ala Ser Tyr Trp Ile Ala Gln Phe Asn Lys Ser Ser
65 70 75

GGT CAC GTG GAT TAT CAT CAC TTT GCT TTT CCG GAT GAA ATT AAA AAT 588
Gly His Val Asp Tyr His His Phe Ala Phe Pro Asp Glu Ile Lys Asn
80 85 90 95

TAT GTT TCA GTG AGT GAA GAA GAA AAG GCT ATT AAT GTG CCT GCT ATT 636
Tyr Val Ser Val Ser Glu Glu Glu Lys Ala Ile Asn Val Pro Ala Ile
100 105 110

-continued

| | | | | | | | | | | | | | | | | |
|---|---|---|---|---|---|---|---|---|---|---|---|---|---|---|---|---|
| ATT | TAT | TTT | GTT | GAA | AAC | GGT | TCA | TGG | GGA | GAT | ATT | ATT | TTT | TAT | ATT | 684 |
| Ile | Tyr | Phe | Val | Glu | Asn | Gly | Ser | Trp | Gly | Asp | Ile | Ile | Phe | Tyr | Ile | |
| | | | 115 | | | | | 120 | | | | | 125 | | | |
| TTC | AAT | GAA | ATG | ATT | TTT | CAT | TCC | GAA | AAA | AGC | AGA | GCA | CTA | GAA | ATA | 732 |
| Phe | Asn | Glu | Met | Ile | Phe | His | Ser | Glu | Lys | Ser | Arg | Ala | Leu | Glu | Ile | |
| | | 130 | | | | | 135 | | | | | 140 | | | | |
| AGT | ACA | TCA | AAT | CAC | AAT | ATG | GCA | TTA | GGC | TTG | AAG | ATT | AAA | GAA | ACT | 780 |
| Ser | Thr | Ser | Asn | His | Asn | Met | Ala | Leu | Gly | Leu | Lys | Ile | Lys | Glu | Thr | |
| | 145 | | | | | 150 | | | | | 155 | | | | | |
| AAA | AAT | GGG | GGG | GAT | TTT | GTC | ATT | CAG | CTT | TAT | GAT | CCC | AAC | CAT | ACA | 828 |
| Lys | Asn | Gly | Gly | Asp | Phe | Val | Ile | Gln | Leu | Tyr | Asp | Pro | Asn | His | Thr | |
| 160 | | | | | 165 | | | | | 170 | | | | | 175 | |
| GCA | ACT | CAT | TTA | CGA | GCA | GAG | TTT | AAC | AAA | TTT | AAC | TTA | GCT | AAA | ATA | 876 |
| Ala | Thr | His | Leu | Arg | Ala | Glu | Phe | Asn | Lys | Phe | Asn | Leu | Ala | Lys | Ile | |
| | | | | 180 | | | | | 185 | | | | | 190 | | |
| AAA | AAA | CTG | ACT | GTA | GAT | AAT | TTT | CTT | GAT | GAA | AAA | CAT | CAG | AAA | TGT | 924 |
| Lys | Lys | Leu | Thr | Val | Asp | Asn | Phe | Leu | Asp | Glu | Lys | His | Gln | Lys | Cys | |
| | | | 195 | | | | | 200 | | | | | 205 | | | |
| TAT | GGT | CTT | ATA | TCC | GAC | GGT | ATG | TCT | ATA | TTT | GTG | GAC | AGA | CAT | ACT | 972 |
| Tyr | Gly | Leu | Ile | Ser | Asp | Gly | Met | Ser | Ile | Phe | Val | Asp | Arg | His | Thr | |
| | | 210 | | | | | 215 | | | | | 220 | | | | |
| CCA | ACA | AGC | ATG | TCC | TCC | ATA | ATC | AGA | TGG | CCT | AAT | AAT | TTA | CTT | CAC | 1020 |
| Pro | Thr | Ser | Met | Ser | Ser | Ile | Ile | Arg | Trp | Pro | Asn | Asn | Leu | Leu | His | |
| | 225 | | | | | 230 | | | | | 235 | | | | | |
| CCC | AAA | GTT | ATT | TAT | CAC | GCG | ATG | CGT | ATG | GGA | TTG | ACT | GAG | CTA | ATC | 1068 |
| Pro | Lys | Val | Ile | Tyr | His | Ala | Met | Arg | Met | Gly | Leu | Thr | Glu | Leu | Ile | |
| 240 | | | | | 245 | | | | | 250 | | | | | 255 | |
| CAA | AAA | GTA | ACA | AGA | GTC | GTA | CAA | CTA | TCT | GAC | CTT | TCA | GAC | AAT | ACG | 1116 |
| Gln | Lys | Val | Thr | Arg | Val | Val | Gln | Leu | Ser | Asp | Leu | Ser | Asp | Asn | Thr | |
| | | | | 260 | | | | | 265 | | | | | 270 | | |
| TTA | GAA | TTA | CTT | TTG | GCA | GCC | AAA | AAT | GAC | GAT | GGT | TTG | TCA | GGA | TTG | 1164 |
| Leu | Glu | Leu | Leu | Leu | Ala | Ala | Lys | Asn | Asp | Asp | Gly | Leu | Ser | Gly | Leu | |
| | | | 275 | | | | | 280 | | | | | 285 | | | |
| CTT | TTA | GCT | TTA | CAA | AAT | GGG | CAT | TCA | GAT | ACA | ATC | TTA | GCA | TAC | GGA | 1212 |
| Leu | Leu | Ala | Leu | Gln | Asn | Gly | His | Ser | Asp | Thr | Ile | Leu | Ala | Tyr | Gly | |
| | | 290 | | | | | 295 | | | | | 300 | | | | |
| GAA | CTC | CTG | GAA | ACT | TCT | GGA | CTT | AAC | CTT | GAT | AAA | ACG | GTA | GAA | CTA | 1260 |
| Glu | Leu | Leu | Glu | Thr | Ser | Gly | Leu | Asn | Leu | Asp | Lys | Thr | Val | Glu | Leu | |
| | 305 | | | | | 310 | | | | | 315 | | | | | |
| CTA | ACT | GCG | GAA | GGA | ATG | GGA | GGA | CGA | ATA | TCG | GGT | TTA | TCC | CAA | GCA | 1308 |
| Leu | Thr | Ala | Glu | Gly | Met | Gly | Gly | Arg | Ile | Ser | Gly | Leu | Ser | Gln | Ala | |
| 320 | | | | | 325 | | | | | 330 | | | | | 335 | |
| CTT | CAA | AAT | GGG | CAT | GCA | GAA | ACT | ATC | AAA | ACA | TAC | GGA | AGG | CTT | CTC | 1356 |
| Leu | Gln | Asn | Gly | His | Ala | Glu | Thr | Ile | Lys | Thr | Tyr | Gly | Arg | Leu | Leu | |
| | | | | 340 | | | | | 345 | | | | | 350 | | |
| AAG | AAG | AGA | GCA | ATA | AAT | ATC | GAA | TAC | AAT | AAG | CTG | AAA | AAT | TTG | CTG | 1404 |
| Lys | Lys | Arg | Ala | Ile | Asn | Ile | Glu | Tyr | Asn | Lys | Leu | Lys | Asn | Leu | Leu | |
| | | | 355 | | | | | 360 | | | | | 365 | | | |
| ACC | GCT | TAT | TAT | TAT | GAT | GAA | GTA | CAC | AGA | CAG | ATA | CCT | GGA | CTA | ATG | 1452 |
| Thr | Ala | Tyr | Tyr | Tyr | Asp | Glu | Val | His | Arg | Gln | Ile | Pro | Gly | Leu | Met | |
| | | 370 | | | | | 375 | | | | | 380 | | | | |
| TTT | GCT | CTT | CAA | AAT | GGA | CAT | GCA | GAT | GCT | ATA | CGC | GCA | TAC | GGT | GAG | 1500 |
| Phe | Ala | Leu | Gln | Asn | Gly | His | Ala | Asp | Ala | Ile | Arg | Ala | Tyr | Gly | Glu | |
| | 385 | | | | | 390 | | | | | 395 | | | | | |
| CTC | ATT | CTT | AGC | CCC | CCT | CTC | CTC | AAC | TCA | GAG | GAT | ATT | GTA | AAT | TTG | 1548 |
| Leu | Ile | Leu | Ser | Pro | Pro | Leu | Leu | Asn | Ser | Glu | Asp | Ile | Val | Asn | Leu | |
| 400 | | | | | 405 | | | | | 410 | | | | | 415 | |
| CTG | GCC | TCA | AGG | AGA | TAT | GAC | AAT | GTT | CCC | GGA | CTT | CTG | TTA | GCA | TTG | 1596 |
| Leu | Ala | Ser | Arg | Arg | Tyr | Asp | Asn | Val | Pro | Gly | Leu | Leu | Leu | Ala | Leu | |
| | | | | 420 | | | | | 425 | | | | | 430 | | |

-continued

AAT AAT GGA CAG GCT GAT GCA ATC TTA GCT TAT GGT GAT ATC TTG AAT 1644
Asn Asn Gly Gln Ala Asp Ala Ile Leu Ala Tyr Gly Asp Ile Leu Asn
435 440 445

GAG GCA AAA CTT AAC TTG GAT AAA AAA GCA GAG CTG TTA GAA GCG AAA 1692
Glu Ala Lys Leu Asn Leu Asp Lys Lys Ala Glu Leu Leu Glu Ala Lys
450 455 460

GAT TCT AAT GGT TTA TCT GGA TTG TTT GTA GCC TTG CAT AAT GGA TGT 1740
Asp Ser Asn Gly Leu Ser Gly Leu Phe Val Ala Leu His Asn Gly Cys
465 470 475

GTA GAA ACA ATT ATT GCT TAT GGG AAA ATA CTT CAC ACT GCA GAC CTT 1788
Val Glu Thr Ile Ile Ala Tyr Gly Lys Ile Leu His Thr Ala Asp Leu
480 485 490 495

ACT CCA CAT CAG GCA TCA AAA TTA CTG GCA GCA GAA GGC CCA AAT GGG 1836
Thr Pro His Gln Ala Ser Lys Leu Leu Ala Ala Glu Gly Pro Asn Gly
500 505 510

GTA TCT GGA TTA ATT ATA GCT TTT CAA AAT AGG AAT TTT GAG GCA ATA 1884
Val Ser Gly Leu Ile Ile Ala Phe Gln Asn Arg Asn Phe Glu Ala Ile
515 520 525

AAA ACT TAT ATG GGA ATA ATA AAA AAT GAA AAT ATT ACA CCT GAA GAA 1932
Lys Thr Tyr Met Gly Ile Ile Lys Asn Glu Asn Ile Thr Pro Glu Glu
530 535 540

ATA GCA GAA CAC TTG GAC AAA AAA AAT GGA AGT GAT TTT CTA GAA ATT 1980
Ile Ala Glu His Leu Asp Lys Lys Asn Gly Ser Asp Phe Leu Glu Ile
545 550 555

ATG AAG AAT ATA AAA AGC TGAATATTAT 2008
Met Lys Asn Ile Lys Ser
560 565

( 2 ) INFORMATION FOR SEQ ID NO:2:

( i ) SEQUENCE CHARACTERISTICS:
( A ) LENGTH: 1722 base pairs
( B ) TYPE: nucleic acid
( C ) STRANDEDNESS: single
( D ) TOPOLOGY: linear ( i i ) MOLECULE TYPE: genomic DNA ( i i i ) HYPOTHETICAL: NO ( i v ) ANTI-SENSE: NO ( v i ) ORIGINAL SOURCE:
( A ) ORGANISM: Shigella flexneri 2a
( B ) STRAIN: M4243

( x i ) SEQUENCE DESCRIPTION: SEQ ID NO:2:

ACCCATCAAT GAAAGGAATA TATA CAT ATG CCA TCA GTA AAT TTA ATC CCA 51
Met Pro Ser Val Asn Leu Ile Pro
1 5

TCA AGG AAA ATA TGT TTG CAA AAT ATG ATA AAT AAA GAC AAC GTC TCT 99
Ser Arg Lys Ile Cys Leu Gln Asn Met Ile Asn Lys Asp Asn Val Ser
10 15 20

GTT GAG ACA ATC CAG TCT CTA TTG CAC TCA AAA CAA TTG CCA TAT TTT 147
Val Glu Thr Ile Gln Ser Leu Leu His Ser Lys Gln Leu Pro Tyr Phe
25 30 35 40

TCT GAC AAG AGG AGT TTT TTA TTA AAT CTA AAT TGC CAA GTT ACC GAT 195
Ser Asp Lys Arg Ser Phe Leu Leu Asn Leu Asn Cys Gln Val Thr Asp
45 50 55

CAC TCT GGA AGA CTT ATT GTC TGT CGA CAT TTA GCT TCC TAC TGG ATA 243
His Ser Gly Arg Leu Ile Val Cys Arg His Leu Ala Ser Tyr Trp Ile
60 65 70

GCA CAG TTT AAC AAA AGT AGT GGT CAC GTG GAT TAT CAT CAC TTT GCT 291

-continued

```
Ala Gln Phe Asn Lys Ser Ser Gly His Val Asp Tyr His His Phe Ala
         75                  80                  85

TTT CCG GAT GAA ATT AAA AAT TAT GTT TCA GTG AGT GAA GAA GAA AAG      339
Phe Pro Asp Glu Ile Lys Asn Tyr Val Ser Val Ser Glu Glu Glu Lys
     90                  95                 100

GCT ATT AAT GTG CCT GCT ATT ATT TAT TTT GTT GAA AAC GGT TCA TGG      387
Ala Ile Asn Val Pro Ala Ile Ile Tyr Phe Val Glu Asn Gly Ser Trp
105                 110                 115                 120

GGA GAT ATT ATT TTT TAT ATT TTC AAT GAA ATG ATT TTT CAT TCC GAA      435
Gly Asp Ile Ile Phe Tyr Ile Phe Asn Glu Met Ile Phe His Ser Glu
                125                 130                 135

AAA AGC AGA GCA CTA GAA ATA AGT ACA TCA AAT CAC AAT ATG GCA TTA      483
Lys Ser Arg Ala Leu Glu Ile Ser Thr Ser Asn His Asn Met Ala Leu
            140                 145                 150

GGC TTG AAG ATT AAA GAA ACT AAA AAT GGG GGG GAT TTT GTC ATT CAG      531
Gly Leu Lys Ile Lys Glu Thr Lys Asn Gly Gly Asp Phe Val Ile Gln
        155                 160                 165

CTT TAT GAT CCC AAC CAT ACA GCA ACT CAT TTA CGA GCA GAG TTT AAC      579
Leu Tyr Asp Pro Asn His Thr Ala Thr His Leu Arg Ala Glu Phe Asn
    170                 175                 180

AAA TTT AAC TTA GCT AAA ATA AAA AAA CTG ACT GTA GAT AAT TTT CTT      627
Lys Phe Asn Leu Ala Lys Ile Lys Lys Leu Thr Val Asp Asn Phe Leu
185                 190                 195                 200

GAT GAA AAA CAT CAG AAA TGT TAT GGT CTT ATA TCC GAC GGT ATG TCT      675
Asp Glu Lys His Gln Lys Cys Tyr Gly Leu Ile Ser Asp Gly Met Ser
                205                 210                 215

ATA TTT GTG GAC AGA CAT ACT CCA ACA AGC ATG TCC TCC ATA ATC AGA      723
Ile Phe Val Asp Arg His Thr Pro Thr Ser Met Ser Ser Ile Ile Arg
            220                 225                 230

TGG CCT GAT AAT TTA CTT CAC CCC AAA GTT ATT TAT CAC GCG ATG CGT      771
Trp Pro Asp Asn Leu Leu His Pro Lys Val Ile Tyr His Ala Met Arg
        235                 240                 245

ATG GGA TTG ACT GAG CTA ATC CAA AAA GTA ACA AGA GTC GTA CAA CTA      819
Met Gly Leu Thr Glu Leu Ile Gln Lys Val Thr Arg Val Val Gln Leu
    250                 255                 260

TCT GAC CTT TCA GAC AAT ACG TTA GAA TTA CTT TTG GCA GCC AAA AAT      867
Ser Asp Leu Ser Asp Asn Thr Leu Glu Leu Leu Leu Ala Ala Lys Asn
265                 270                 275                 280

GAC GAT GGT TTG TCA GGA TTG CTT TTA GCT TTA CAA AAT GGG CAT TCA      915
Asp Asp Gly Leu Ser Gly Leu Leu Leu Ala Leu Gln Asn Gly His Ser
                285                 290                 295

GAT ACA ATC TTA GCA TAC GGA GAA CTC TTG GAA ACT TCT GGA CTT AAC      963
Asp Thr Ile Leu Ala Tyr Gly Glu Leu Leu Glu Thr Ser Gly Leu Asn
            300                 305                 310

CTT GAT AAA ACG GTA GAA CTA CTA ACT GCG GAA GGA ATG GGA GGA CGA     1011
Leu Asp Lys Thr Val Glu Leu Leu Thr Ala Glu Gly Met Gly Gly Arg
        315                 320                 325

ATA TCG GGT TTA TCC CAA GCA CTT CAA AAT GGG CAT GCA GAA ACT ATC     1059
Ile Ser Gly Leu Ser Gln Ala Leu Gln Asn Gly His Ala Glu Thr Ile
    330                 335                 340

AAA ACA TAC GGA AGG CTT CTC AAG AAG AGA GCA ATA AAT ATC GAA TAC     1107
Lys Thr Tyr Gly Arg Leu Leu Lys Lys Arg Ala Ile Asn Ile Glu Tyr
345                 350                 355                 360

AAT AAG CTG AAA AAT TTG CTG ACC GCT TAT TAT TAT GAT GAA GTA CAC     1155
Asn Lys Leu Lys Asn Leu Leu Thr Ala Tyr Tyr Tyr Asp Glu Val His
                365                 370                 375

AGA CAG ATA CCC GGA CTA ATG TTT GCT CTT CAA AAT GGA CAT GCA GAT     1203
Arg Gln Ile Pro Gly Leu Met Phe Ala Leu Gln Asn Gly His Ala Asp
            380                 385                 390
```

-continued

GCT ATA CGC GCA TAC GGT GAG CTC ATT CTT AGC CCC CCT CTC CTC AAC 1251
Ala Ile Arg Ala Tyr Gly Glu Leu Ile Leu Ser Pro Pro Leu Leu Asn
395 400 405

TCA GAG GAT ATT GTA AAT TTG CTG GCC TCA AGG AGA TAT GAC AAT GTT 1299
Ser Glu Asp Ile Val Asn Leu Leu Ala Ser Arg Arg Tyr Asp Asn Val
410 415 420

CCC GGA CTT CTG TTA GCA TTG AAT AAT GGA CAG GCT GAT GCA ATC TTA 1347
Pro Gly Leu Leu Leu Ala Leu Asn Asn Gly Gln Ala Asp Ala Ile Leu
425 430 435 440

GCT TAT GGT GAT ATC TTG AAT GAG GCA AAA CTT AAC TTG GAT AAA AAA 1395
Ala Tyr Gly Asp Ile Leu Asn Glu Ala Lys Leu Asn Leu Asp Lys Lys
445 450 455

GCA GAG CTG TTA GAA GCG AAA GAT TCT AAT GGT TTA TCT GGA TTG TTT 1443
Ala Glu Leu Leu Glu Ala Lys Asp Ser Asn Gly Leu Ser Gly Leu Phe
460 465 470

GTA GCC TTG CAT AAT GGA TGT GTA GAA ACA ATT ATT GCT TAT GGG AAA 1491
Val Ala Leu His Asn Gly Cys Val Glu Thr Ile Ile Ala Tyr Gly Lys
475 480 485

ATA CTT CAC ACT GCA GAC CTT ACT CCA CAT CAG GCA TCA AAA TTA CTG 1539
Ile Leu His Thr Ala Asp Leu Thr Pro His Gln Ala Ser Lys Leu Leu
490 495 500

GCA GCA GAA GGC CCA AAT GGG GTA TCT GGA TTA ATT ATA GCT TTT CAA 1587
Ala Ala Glu Gly Pro Asn Gly Val Ser Gly Leu Ile Ile Ala Phe Gln
505 510 515 520

AAT AGG AAT TTT GAG GCA ATA AAA ACT TAT ATG AAA ATA ATA AAA AAT 1635
Asn Arg Asn Phe Glu Ala Ile Lys Thr Tyr Met Lys Ile Ile Lys Asn
525 530 535

GAA AAT ATT ACA CCT GAA GAA ATA GCA GAA CAC TTG GAC AAA AAA AAT 1683
Glu Asn Ile Thr Pro Glu Glu Ile Ala Glu His Leu Asp Lys Lys Asn
540 545 550

GGA AGT GAT TTT CTA GAA ATT ATG AAG AAT ATA AAA AGC 1722
Gly Ser Asp Phe Leu Glu Ile Met Lys Asn Ile Lys Ser
555 560 565

( 2 ) INFORMATION FOR SEQ ID NO:3:

( i ) SEQUENCE CHARACTERISTICS:
( A ) LENGTH: 4 amino acids
( B ) TYPE: amino acid
( C ) STRANDEDNESS: unknown
( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: N-terminal fragment ( x i ) SEQUENCE DESCRIPTION: SEQ ID NO:3:

Ala Pro Pro Val 4

( 2 ) INFORMATION FOR SEQ ID NO:4:

( i ) SEQUENCE CHARACTERISTICS:
( A ) LENGTH: 14amino acids
( B ) TYPE: amino acid
( C ) STRANDEDNESS: unknown
( D ) TOPOLOGY: linear ( i i ) MOLECULE TYPE: peptide ( i i i ) HYPOTHETICAL: NO ( i v ) ANTI-SENSE: NO -continued ( v ) FRAGMENT TYPE: N-terminal fragment ( x i ) SEQUENCE DESCRIPTION: SEQ ID NO:4:

Ala Pro Pro Val Pro Ile Asn Pro Ala Xaa Pro Ile Xaa Arg 14

( 2 ) INFORMATION FOR SEQ ID NO:5:

( i ) SEQUENCE CHARACTERISTICS:
( A ) LENGTH: 29 base pairs
( B ) TYPE: nucleic acid
( C ) STRANDEDNESS: single
( D ) TOPOLOGY: linear ( i i ) MOLECULE TYPE: synthetic DNA ( i i i ) HYPOTHETICAL: NO ( i v ) ANTI-SENSE: NO ( x i ) SEQUENCE DESCRIPTION: SEQ ID NO:5:

TAATCGAATT CATGGAATCC CTGACGTTA 29

( 2 ) INFORMATION FOR SEQ ID NO:6:

( i ) SEQUENCE CHARACTERISTICS:
( A ) LENGTH: 42 base pairs
( B ) TYPE: nucleic acid
( C ) STRANDEDNESS: single
( D ) TOPOLOGY: linear ( i i ) MOLECULE TYPE: synthetic DNA ( i i i ) HYPOTHETICAL: NO ( i v ) ANTI-SENSE: NO ( x i ) SEQUENCE DESCRIPTION: SEQ ID NO:6:

GGTACCCCCA ATATTAGGGC CATCAACGTC AACGTTGCCG CC 42

( 2 ) INFORMATION FOR SEQ ID NO:7:

( i ) SEQUENCE CHARACTERISTICS:
( A ) LENGTH: 42 base pairs
( B ) TYPE: nucleic acid
( C ) STRANDEDNESS: single
( D ) TOPOLOGY: linear ( i i ) MOLECULE TYPE: synthetic DNA ( i i i ) HYPOTHETICAL: NO ( i v ) ANTI-SENSE: NO ( x i ) SEQUENCE DESCRIPTION: SEQ ID NO:7:

AATATTGGGG GTACCGGTAC TTATTTGGTC GAAGGCGATG CA 42

( 2 ) INFORMATION FOR SEQ ID NO:8:

( i ) SEQUENCE CHARACTERISTICS:
( A ) LENGTH: 30 base pairs
( B ) TYPE: nucleic acid
( C ) STRANDEDNESS: single
( D ) TOPOLOGY: linear ( i i ) MOLECULE TYPE: synthetic DNA ( i i i ) HYPOTHETICAL: NO ( i v ) ANTI-SENSE: NO -continued ( x i ) SEQUENCE DESCRIPTION: SEQ ID NO:8:

TGATAAGTCG ACTCAGGCTG CCTGGCTAAT 30

( 2 ) INFORMATION FOR SEQ ID NO:9:

( i ) SEQUENCE CHARACTERISTICS:
( A ) LENGTH: 30 base pairs
( B ) TYPE: nucleic acid
( C ) STRANDEDNESS: single
( D ) TOPOLOGY: linear ( i i ) MOLECULE TYPE: synthetic DNA ( i i i ) HYPOTHETICAL: NO ( i v ) ANTI-SENSE: NO ( x i ) SEQUENCE DESCRIPTION: SEQ ID NO:9:

GGGGAATTCC AAATTCACAA ATTTTTTTGT 30

( 2 ) INFORMATION FOR SEQ ID NO:10:

( i ) SEQUENCE CHARACTERISTICS:
( A ) LENGTH: 30 base pairs
( B ) TYPE: nucleic acid
( C ) STRANDEDNESS: single
( D ) TOPOLOGY: linear ( i i ) MOLECULE TYPE: synthetic DNA ( i i i ) HYPOTHETICAL: NO ( i v ) ANTI-SENSE: NO ( x i ) SEQUENCE DESCRIPTION: SEQ ID NO:10:

TCCATGCCAT TCATGGAGTA TTAATGAATT 30

( 2 ) INFORMATION FOR SEQ ID NO:11:

( i ) SEQUENCE CHARACTERISTICS:
( A ) LENGTH: 29 base pairs
( B ) TYPE: nucleic acid
( C ) STRANDEDNESS: single
( D ) TOPOLOGY: linear ( i i ) MOLECULE TYPE: synthetic DNA ( i i i ) HYPOTHETICAL: NO ( i v ) ANTI-SENSE: NO ( x i ) SEQUENCE DESCRIPTION: SEQ ID NO:11:

CTCCATGAAT GGCATGGAAA GGCGGAATA 29

( 2 ) INFORMATION FOR SEQ ID NO:12:

( i ) SEQUENCE CHARACTERISTICS:
( A ) LENGTH: 33 base pairs
( B ) TYPE: nucleic acid
( C ) STRANDEDNESS: single
( D ) TOPOLOGY: linear ( i i ) MOLECULE TYPE: synthetic DNA ( i i i ) HYPOTHETICAL: NO ( i v ) ANTI-SENSE: NO ( x i ) SEQUENCE DESCRIPTION: SEQ ID NO:12:

CGGGTCGACT CAGAAGGTAT ATTTCACACC CAA 33

-continued ( 2 ) INFORMATION FOR SEQ ID NO:13:

( i ) SEQUENCE CHARACTERISTICS:
( A ) LENGTH: 17 base pairs
( B ) TYPE: nucleic acid
( C ) STRANDEDNESS: single
( D ) TOPOLOGY: linear ( i i ) MOLECULE TYPE: synthetic DNA ( i i i ) HYPOTHETICAL: NO ( i v ) ANTI-SENSE: NO ( x i ) SEQUENCE DESCRIPTION: SEQ ID NO:13:

CAGTGTATCA CCACGAG 17

( 2 ) INFORMATION FOR SEQ ID NO:14:

( i ) SEQUENCE CHARACTERISTICS:
( A ) LENGTH: 17 base pairs
( B ) TYPE: nucleic acid
( C ) STRANDEDNESS: single
( D ) TOPOLOGY: linear ( i i ) MOLECULE TYPE: synthetic DNA ( i i i ) HYPOTHETICAL: NO ( i v ) ANTI-SENSE: NO ( x i ) SEQUENCE DESCRIPTION: SEQ ID NO:14:

AAATTATCTA CAGTCAG 17